(12) United States Patent
Cam et al.

(10) Patent No.: US 10,881,487 B2
(45) Date of Patent: Jan. 5, 2021

(54) INSERTABLE AND PREFABRICATED ATTACHMENTS FOR AN ORAL APPLIANCE

(71) Applicant: Align Technology, Inc., San Jose, CA (US)

(72) Inventors: Bruce Cam, San Jose, CA (US); Crystal Tjhia, Sunnyvale, CA (US); Rohit Tanugula, San Jose, CA (US); Dennis Te, San Jose, CA (US)

(73) Assignee: Align Technology, Inc., San Jose, CA (US)

(*) Notice: Subject to any disclaimer, the term of this patent is extended or adjusted under 35 U.S.C. 154(b) by 0 days.

(21) Appl. No.: 15/199,598

(22) Filed: Jun. 30, 2016

(65) Prior Publication Data
US 2018/0000564 A1    Jan. 4, 2018

(51) Int. Cl.
| | | |
|---|---|---|
| *A61C 7/08* | (2006.01) | |
| *A61C 7/14* | (2006.01) | |
| *A61C 7/36* | (2006.01) | |
| *B33Y 10/00* | (2015.01) | |
| *B33Y 80/00* | (2015.01) | |

(Continued)

(52) U.S. Cl.
CPC .............. *A61C 7/08* (2013.01); *A61C 7/14* (2013.01); *A61C 7/36* (2013.01); *A61F 5/566* (2013.01); *A63B 71/085* (2013.01); *B29C 51/00* (2013.01); *B29C 51/268* (2013.01); *B29C 64/112* (2017.08); *B29C 65/08* (2013.01); *B29C 65/16* (2013.01); *B29C 69/001* (2013.01); *B33Y 10/00* (2014.12); *B33Y 80/00* (2014.12)

(58) Field of Classification Search
CPC .... A61C 7/08; A61C 7/14; A61C 7/36; B33Y 10/00; B33Y 80/00; B29C 51/00; B29C 51/268; B29C 65/08; B29C 65/16; B29C 67/0059; B29C 69/001; B29C 51/12
USPC ........................................................ 264/510
See application file for complete search history.

(56) References Cited

U.S. PATENT DOCUMENTS

| | | | | |
|---|---|---|---|---|
| 4,360,341 A | * | 11/1982 | Dellinger | .............. A61C 7/146 |
| | | | | 433/24 |
| 4,793,803 A | * | 12/1988 | Martz | ..................... A61C 7/08 |
| | | | | 433/6 |

(Continued)

FOREIGN PATENT DOCUMENTS

| | | |
|---|---|---|
| CN | 203943700 U | 11/2014 |
| DE | 102004007008 A1 | 9/2005 |

(Continued)

OTHER PUBLICATIONS

PCT International Search Report and Written Opinion of the International Searching Authority for PCT/US2017/035825 dated Aug. 24, 2017.

(Continued)

*Primary Examiner* — Heidi M Eide
*Assistant Examiner* — Drew S Folgmann
(74) *Attorney, Agent, or Firm* — Lowenstein Sandler LLP

(57) ABSTRACT

A plastic shell such as an orthodontic aligner has an interior shape that substantially conforms to a current or future dental arch of a patient. The plastic shell includes a hollow feature comprising a cavity. The plastic shell additionally includes an object inserted into the cavity, wherein the object provides structural strength to the plastic shell at a location of the hollow feature and does not interfere with a fit of the plastic shell onto the dental arch of the patient.

20 Claims, 19 Drawing Sheets

(51) Int. Cl.
*B29C 64/112* (2017.01)
*B29C 51/00* (2006.01)
*B29C 65/08* (2006.01)
*B29C 65/16* (2006.01)
*A61F 5/56* (2006.01)
*A63B 71/08* (2006.01)
*B29C 51/26* (2006.01)
*B29C 69/00* (2006.01)

(56) References Cited

U.S. PATENT DOCUMENTS

| | | | | |
|---|---|---|---|---|
| 5,055,039 | A * | 10/1991 | Abbatte | A61C 7/146 433/24 |
| 5,186,623 | A * | 2/1993 | Breads | A61C 7/08 433/214 |
| 6,293,790 | B1 | 9/2001 | Hilliard | |
| 6,554,613 | B1 * | 4/2003 | Sachdeva | A61C 7/00 433/24 |
| 7,059,850 | B1 * | 6/2006 | Phan | A61C 7/00 433/24 |
| 7,845,938 | B2 * | 12/2010 | Kim | A61C 7/146 433/3 |
| 8,025,063 | B2 | 9/2011 | Sotos et al. | |
| 2003/0190575 | A1 | 10/2003 | Hilliard | |
| 2003/0207224 | A1 * | 11/2003 | Lotte | A61C 7/08 433/6 |
| 2005/0233276 | A1 * | 10/2005 | Kopelman | A61C 7/08 433/3 |
| 2006/0177789 | A1 * | 8/2006 | O'Bryan | A61C 7/08 433/6 |
| 2006/0257821 | A1 * | 11/2006 | Cinader, Jr. | A61C 7/146 433/213 |
| 2007/0259303 | A1 * | 11/2007 | Tsukuma | A61C 7/14 433/10 |
| 2010/0138025 | A1 * | 6/2010 | Morton | A61C 7/00 700/104 |
| 2011/0005527 | A1 * | 1/2011 | Andrew | A61C 7/08 128/848 |
| 2012/0295211 | A1 | 11/2012 | Frantz et al. | |
| 2013/0089828 | A1 * | 4/2013 | Borovinskih | A61C 7/08 433/6 |
| 2013/0230819 | A1 | 9/2013 | Arruda | |
| 2015/0238284 | A1 | 8/2015 | Wu et al. | |
| 2015/0335404 | A1 | 11/2015 | Webber et al. | |
| 2015/0336299 | A1 | 11/2015 | Tanugula et al. | |
| 2016/0106521 | A1 | 4/2016 | Tanugula et al. | |
| 2016/0128803 | A1 | 5/2016 | Webber et al. | |
| 2016/0361139 | A1 | 12/2016 | Webber et al. | |

FOREIGN PATENT DOCUMENTS

| | | |
|---|---|---|
| EP | 2 000 111 A1 | 12/2008 |
| EP | 2 886 077 A1 | 6/2015 |

\* cited by examiner

INSERTABLE AND PREFABRICATED ATTACHMENTS FOR AN ORAL APPLIANCE

TECHNICAL FIELD

Embodiments of the present invention relate to the field of orthodontics and dentistry and, in particular, to plastic orthodontic aligners and other plastic shells.

BACKGROUND

For some applications, shells are formed around molds to achieve a negative of the mold. The shells are then removed from the molds to be further used for various applications. One example application in which a shell is formed around a mold and then later used is corrective dentistry or orthodontic treatment. In such an application, the mold is of a dental arch for a patient and the shell is an aligner to be used for aligning one or more teeth of the patient.

One challenge with molds used to form shells is the subsequent removal of the shells from the molds. In order to ensure that a shell will be removable from a mold without damaging or permanently deforming the shell, the shapes and types of features that are included in the mold may be limited. For example, features with significant undercuts (also referred to as negative inclination) and/or complex features may impair the removal of the shell from the mold.

BRIEF DESCRIPTION OF THE DRAWINGS

The present invention is illustrated by way of example, and not by way of limitation, in the figures of the accompanying drawings.

DETAILED DESCRIPTION

Figure 1A:
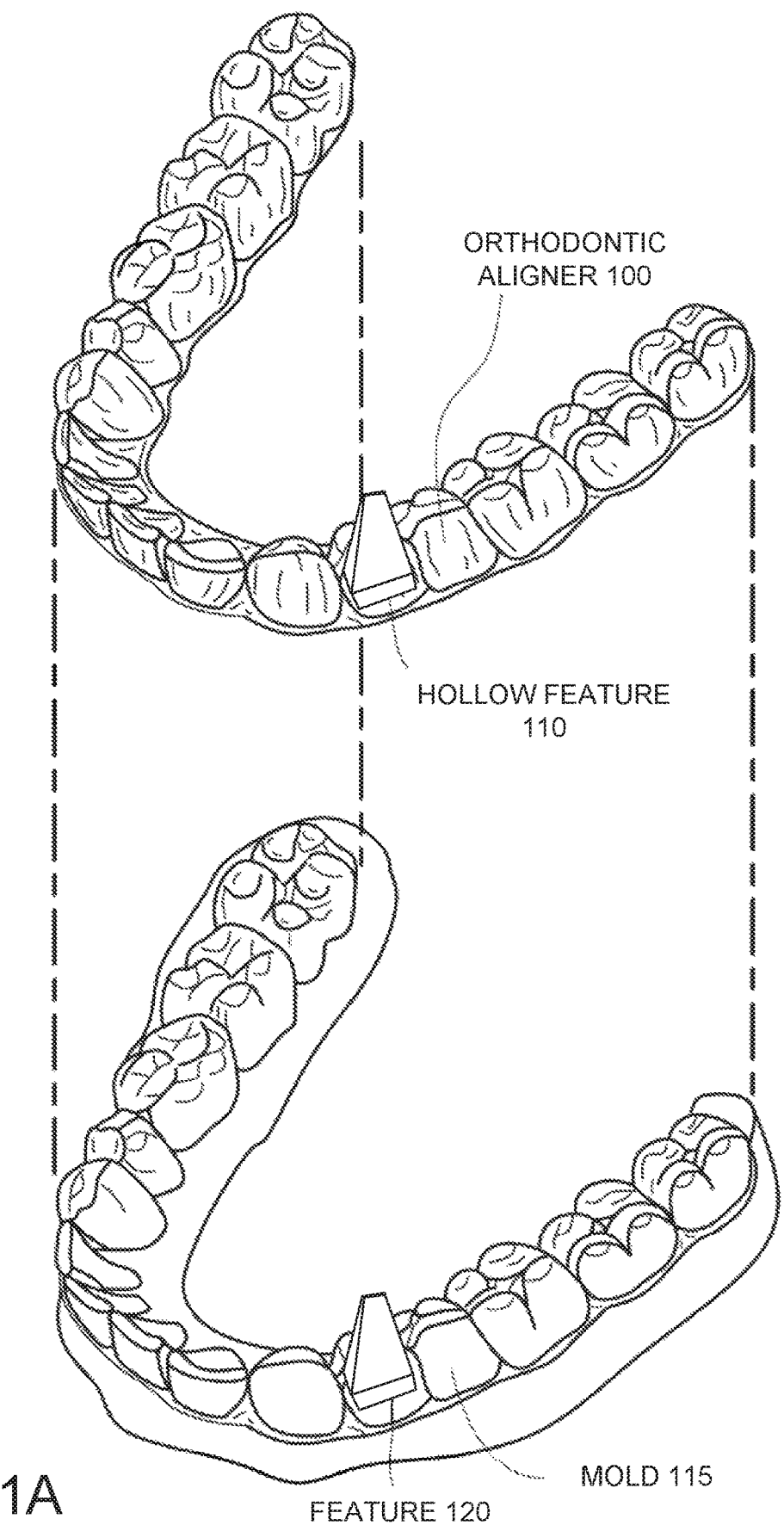
FIG. 1A illustrates an orthodontic aligner and a mold, in accordance with one embodiment.

There are numerous orthodontic appliances that are traditionally used to correct different patient dental conditions. These various types of orthodontic appliances may be used to correct different types and severities of malocclusion (defined as abnormal alignment of the teeth and the way that the upper and lower teeth fit together). For example, orthodontic brackets (also known as braces) may be used with wires to correct some types of malocclusions. Conventional plastic orthodontic aligners may also be used to correct some types of malocclusions. However, some malocclusions may not be treatable using braces or conventional plastic orthodontic aligners. Additionally, some malocclusions may be treatable, but treatment of these malocclusions using current techniques for manufacturing plastic orthodontic aligners may introduce undesirable tradeoffs. For example, some aligner features for mandibular repositioning may have lower strength as compared to a twin block. For such malocclusions, additional orthodontic appliances that may be used on a patient include headgear, expansion appliances (e.g., a palatal expander), spacers, bite plates, Carrier® Distalizers™, functional appliances (e.g., an Andresen appliance, a Bionator, a Hawley retainer, a twin block, a Herbst appliance, a Forsus appliance, etc.), and so on. Additionally, other types of dental appliances may be used on patients for the treatment of sleep apnea and other conditions.

Current plastic aligners may introduce tradeoffs when used to correct malocclusions that are traditionally corrected through the use of some of the aforementioned additional orthodontic appliances. For example, current plastic aligners may be susceptible to crushing when used for some geometries such as large undercuts or complex features. Described herein are embodiments of orthodontic aligners having features that enable the orthodontic aligners to apply forces to correct malocclusions that would traditionally be treated using one or more of the aforementioned additional orthodontic appliances. These features may be hollow features that would ordinarily be susceptible to being crushed. Additionally, the features may have shapes (e.g., large undercuts) that do not permit separation of the orthodontic aligner from a mold that it is formed over at a location of the feature. Accordingly, in embodiments cavities of the features are at least partially filled with objects that may provide structural strength to the features to prevent them from being crushed or otherwise damaged. Insertion of the objects into the hollow features may additionally or alternatively improve hygiene associated with the plastic aligner. The objects may also provide other benefits and/or perform other functions in addition to or instead of providing structural strength. For example, objects of different sizes may be inserted into holes in the features to adjust a patient's bite. Ball ended rods (also referred to herein as rods with attached spheres) may also be placed into holes and/or slots in the features to control articulation of a patient's jaw. The features and objects may also be used for numerous other purposes, such as jaw repositioning, to create joints in the plastic aligner, to alter mechanical properties of the plastic aligner, to alter occlusal contacts, to treat temporomandibular joint disorder (TMD), to enable linkages and/or locks to be applied to plastic aligners, and so on.

An orthodontic aligner as described herein may be included in a series of orthodontic aligners so as to provide an orthodontic system for positioning teeth. Such an orthodontic system can include a sequence of orthodontic aligners each including a shell (e.g., a plastic shell) having a one or more regions shaped to receive at least portions of teeth. The orthodontic aligners may be successively worn by a patient to move one or more teeth from a first arrangement to a second arrangement. One or more of the orthodontic aligners may include hollow features that are at least partially filled with additional objects.

Embodiments are discussed herein with regards to orthodontic aligners. However, embodiments discussed with reference to orthodontic aligners are also applicable to other shells that are used for other purposes, such as orthodontic retainers, orthodontic splints, shells to be used as night guards, shells that are to be used to treat sleep apnea, and so on. Accordingly, it should be understood that any reference to orthodontic aligners also applies to other types of shells (e.g., other types of shells such as orthodontic retainers, orthodontic splints, or other shells that fit onto a patient's teeth but that do not reposition the patient's teeth or jaw).

Turning now to the drawings, FIG. 1A illustrates an example orthodontic aligner 100, which is a tooth and/or jaw repositioning appliance that can be worn by a patient in order to achieve an incremental repositioning of individual teeth in the jaw. The orthodontic aligner 100 can include a shell (e.g., a translucent polymeric shell) having teeth-receiving cavities that receive and resiliently reposition the teeth. The orthodontic aligner 100 or portion(s) thereof may be indirectly fabricated using a physical model or mold 115 of a dental arch including the teeth. For example, an orthodontic aligner can be formed using a physical mold 115 and a sheet of suitable layers of polymeric material. In some instances, an orthodontic aligner 100 is directly fabricated, e.g., using rapid prototyping fabrication techniques, from a digital model of an aligner.

One or more features 120 may be added to the mold 115 that do not represent a patient's teeth. These may be referred to as non-native features, and do not reflect any portion of the patient's dental arch. The feature 120 may be added to a digital representation of the mold 115, and the mold 115 may be fabricated to include the feature 120. Alternatively, the mold 115 may be fabricated without the feature 120 and the feature 120 may be attached to the mold 115 after the mold 115 is manufactured. Many different types of features may be added, one of which is illustrated in FIG. 1A. Features 120 may have any imaginable shape, size, orientation, etc. that is appropriate for insertion into a patient's mouth.

In some embodiments, the mold 115 may be fabricated with a registration feature. In such embodiments the feature 120 may be an object that is attached to the mold via the registration feature.

The orthodontic aligner 100 that is formed over the mold 115 has a shape that conforms to the mold 115. Since the mold 115 is based on a dental arch of the patient, the orthodontic aligner 100 may also conform to and fit over the patient's dental arch. The orthodontic aligner 100 includes a hollow feature 110 having a size, shape, location and orientation based on the feature 120. The hollow feature 110 may be used for many different purposes, such as to apply forces appropriate to perform the operations of one or more of the aforementioned additional orthodontic appliances. In order to improve a structural strength of the hollow feature 110, the feature 120 may detach from the mold 115 and remain inside of the hollow feature 110 in the orthodontic aligner 100 when the orthodontic aligner 100 is removed from the mold 115. Alternatively, an additional object may be inserted into a cavity in the hollow feature 110 after the orthodontic aligner 100 is removed from the mold 115 to at least partially fill the cavity.

Figure 1B:
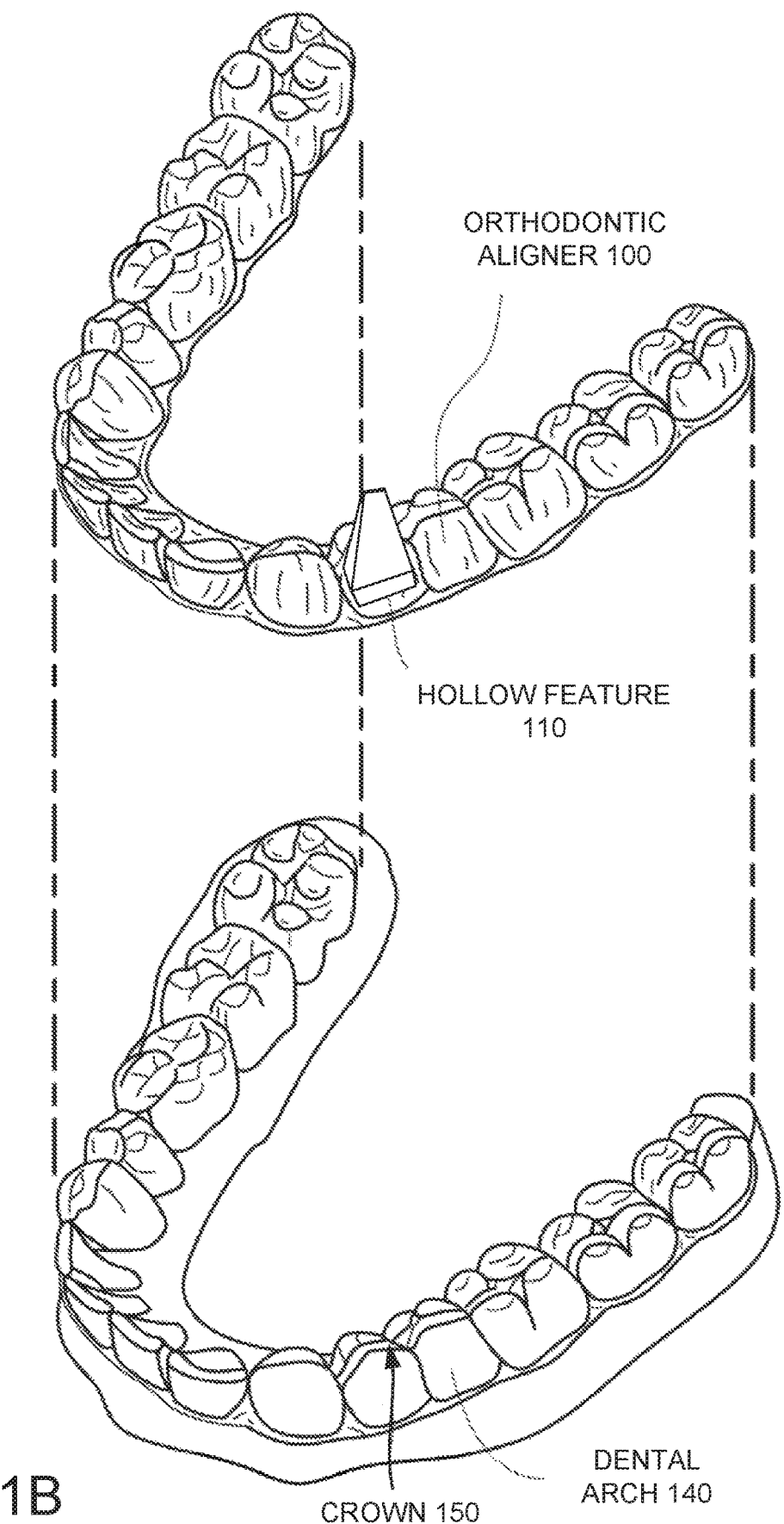
FIG. 1B illustrates an orthodontic aligner and a dental arch, in accordance with one embodiment.

FIG. 1B illustrates an orthodontic aligner 100 and a dental arch 140 of a patient, in accordance with one embodiment. After the orthodontic aligner 100 has been formed and an object has been inserted into or retained in the orthodontic aligner 100, the orthodontic aligner 100 may be positioned onto the dental arch 140 of the patient. The orthodontic aligner 100 can fit over all teeth present in an upper or lower jaw, or less than all of the teeth. The orthodontic aligner 100 can be designed specifically to accommodate the teeth of the patient (e.g., the topography of the tooth-receiving cavities matches the topography of the patient's teeth), and may be fabricated based on positive or negative models of the patient's teeth generated by impression, scanning, and the like. Alternatively, the orthodontic aligner 100 can be a generic aligner configured to receive the teeth, but not necessarily shaped to match the topography of the patient's teeth.

In some cases, only certain teeth received by an orthodontic aligner will be repositioned by the orthodontic aligner while other teeth can provide a base or anchor region for holding the appliance in place as it applies force against the tooth or teeth targeted for repositioning. In some cases, many or most, and even all, of the teeth will be repositioned at some point during treatment. Teeth that are moved can also serve as a base or anchor for holding the orthodontic aligner as it is worn by the patient. Typically, no wires or other means will be provided for holding an aligner in place over the teeth. In some cases, however, it may be desirable to provide individual attachments or other anchoring elements (not shown) on teeth with corresponding receptacles or apertures (not shown) in the orthodontic aligner 100 so that the orthodontic aligner can apply a selected force on the tooth.

As shown, the orthodontic aligner 100 includes a hollow feature 110 that is at least partially filled with an object (not shown). The object is shaped so as not to interfere with a fit of the orthodontic aligner 100 over the dental arch of the patient. As shown, the patient's dental arch 140 does not include the feature 120 that was used to create hollow feature 110. Instead, the dental arch 140 includes a crown 150 of a tooth at a location corresponding to the location of the feature 120. The object inside of the hollow feature 110 may have a shape that conforms to a contour of the crown 150. Alternatively, the object may be slightly recessed into the hollow feature and may not contact the crown 150 when the orthodontic aligner 100 is positioned onto the patient's dental arch 140.

FIGS. 2A-7C illustrate numerous examples of plastic shells such as plastic orthodontic aligners that have hollow features with cavities that are at least partially filled with an object. The object may be separate from the plastic shell, but may be secured to the plastic shell by friction, a mechanical registration feature, a bond or weld, or other mechanism. The object may be made of the same material as the plastic shell or of a different material than the plastic shell. For example, the object may be a different type of plastic from the plastic shell. The object may also be, for example, metal, a ceramic, dental cement, a dental composite material, a two phase polymer, epoxy, and so on. The object may be a solid object (e.g., lacking gaps or voids), may be a mesh (e.g., a wire mesh), or may be a frame having struts, webbing, etc. The objects may be custom or stock prefabricated objects or may be objects that were injected into the cavities of the hollow features as a liquid phase and then solidified to form the objects.

Figure 2A:
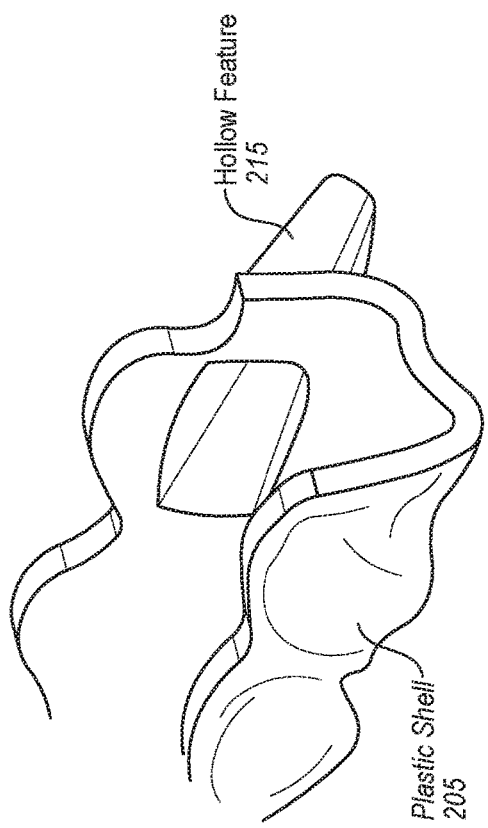
FIG. 2A illustrates a cross sectional side view of a plastic shell over a mold, in accordance with one embodiment.
Figure 2C:
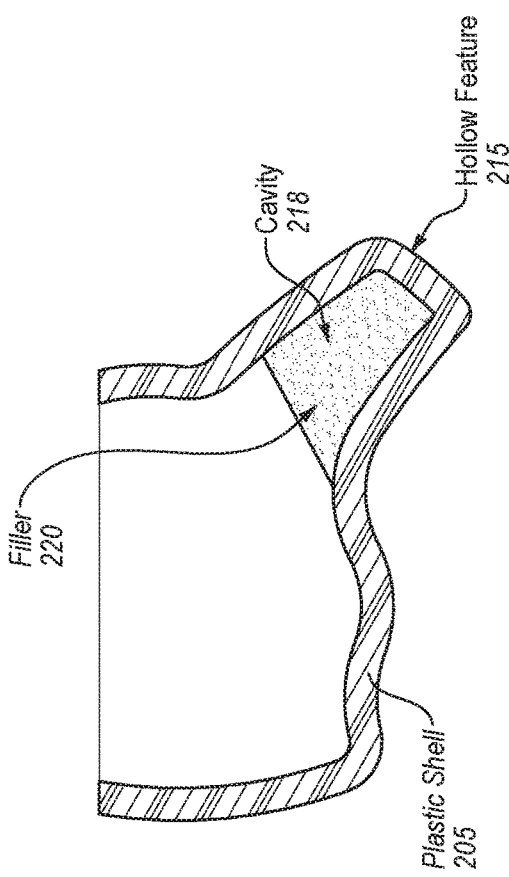
FIG. 2C illustrates a perspective view of a portion of the plastic shell of FIG. 2B, in accordance with one embodiment.
Figure 2B:
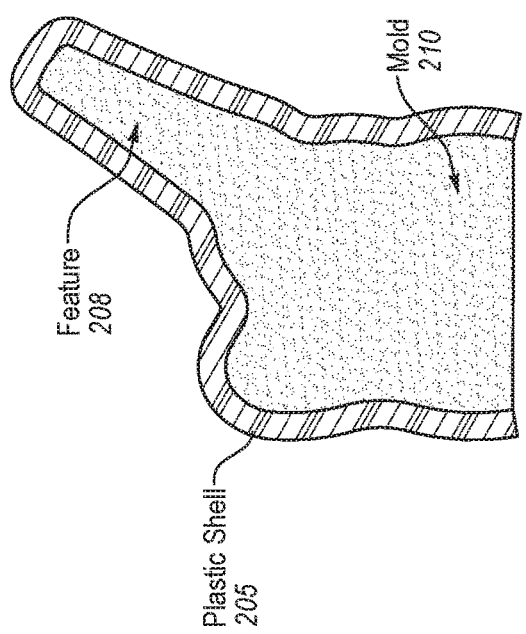
FIG. 2B illustrates a cross sectional side view of the plastic shell of FIG. 2A removed from the mold, in accordance with one embodiment.

FIGS. 2A-2F illustrate various embodiments of a plastic shell having a hollow feature that is at least partially filled using a liquid phase material that is then cured to transform the liquid phase material into a solid phase material. FIG. 2A illustrates a cross sectional side view of a plastic shell 205 over a mold 210, in accordance with one embodiment. The mold 210 includes a feature 208 that does not correspond to any region of a patient's dental arch. FIG. 2B illustrates a cross sectional side view of the plastic shell 205 of FIG. 2A removed from the mold 210, in accordance with one embodiment. As shown, the plastic shell 205 includes a hollow feature 215 having a cavity 218, the hollow feature 215 having been formed as a result of forming the plastic shell 205 over feature 208. FIG. 2C illustrates a perspective view of a portion of the plastic shell 205 of FIG. 2B including the hollow feature 215, in accordance with one embodiment.

Figure 2D:
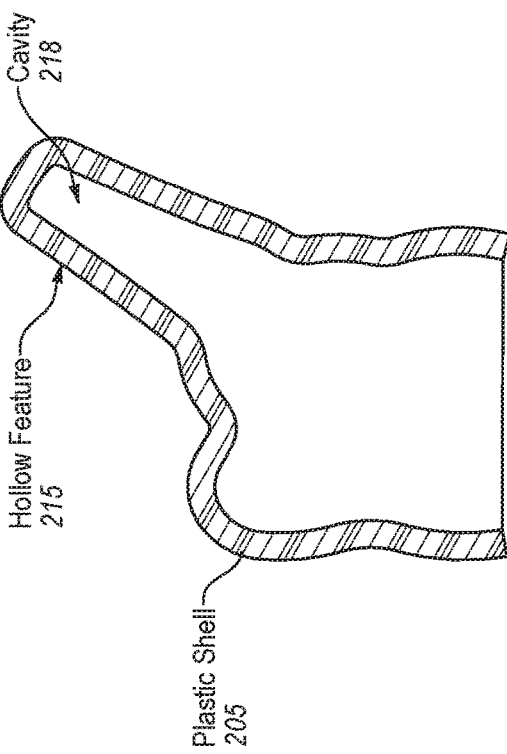
FIG. 2D illustrates a cross sectional side view of the plastic shell of FIG. 2B after a cavity of a hollow feature has been filled by a filler, in accordance with one embodiment.

FIG. 2D illustrates a cross sectional side view of the plastic shell 205 of FIG. 2B after the cavity 218 of the hollow feature 215 has been filled by a filler 220, in accordance with one embodiment. The filler 220 may be injected into the cavity 218 from an underside of the plastic shell 205. Enough of the filler 220 may be injected into the cavity 218 to substantially fill the cavity 218 without interfering with a fit of the plastic shell 205 onto a patient's tooth (e.g., without interfering with the occlusal surface of a crown underlying the hollow feature 215 when the plastic shell 205 is worn by the patient).

The filler 220 may be a two phase material that is in a liquid phase when injected into the cavity 218. The filler 220 may then be cured to transform the liquid phase material into a solid phase material. Examples of materials that may be used include a two phase plastic, an epoxy, dental cement, a dental composite, and so on. Depending on the material used for the filler 220, the liquid phase material may be cured by application of heat, ultraviolet (UV) light, air, pressure, and so on. Some materials such as epoxy may start as two separate liquids that are mixed and that automatically transform into a solid a predetermined amount of time after the mixing. The cavity 218 may have a shape with one or more undercuts, ledges, lips, knurling or other features that will cause the filler 220 (which becomes an object when cured) to be mechanically interlocked with the hollow feature 215. Thus, the filler 220 may not be removable from the plastic shell 205 after the filler 220 is transformed into the solid phase.

Figure 2E:
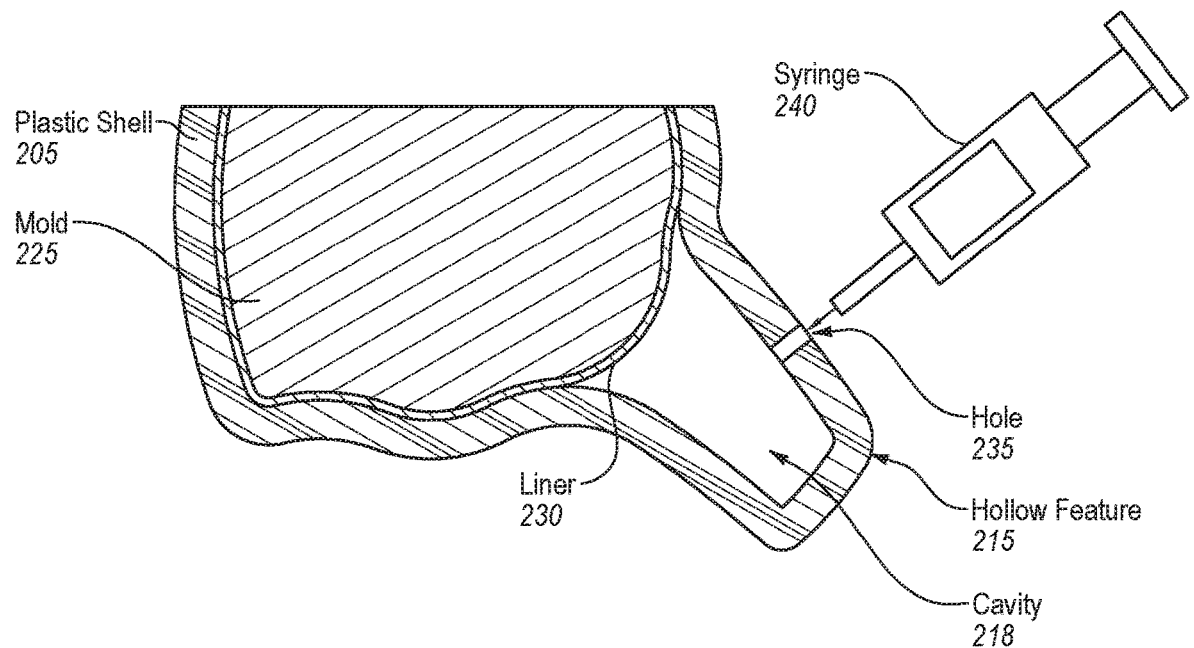
FIG. 2E illustrates a cross sectional side view of the plastic shell of FIG. 2B after the plastic shell has been placed over a second mold, in accordance with one embodiment.

FIG. 2E illustrates a cross sectional side view of the plastic shell 205 of FIG. 2B after the plastic shell 205 has been placed over a second mold 225, in accordance with one embodiment. In some instances it may be desirable for a shape of the object formed in the cavity 218 of the hollow feature 215 to conform to a contour of a tooth crown that will underlie the hollow feature 215. Accordingly, the plastic shell 205 may be placed onto the second mold 225.

The second mold 225 may be substantially similar to the mold 210 used to form the plastic shell 205. However, the second mold 225 may not include the feature that caused the hollow feature 215 to be formed. Instead, the second mold 225 may have the shape of a crown at a location corresponding to the location of the feature in the mold 210.

A hole 235 may be drilled into the hollow feature 215. The hole 235 may terminate at the cavity 218. A syringe 238 or other applicator may be used to inject a liquid phase material (filler) into the cavity 218 through the hole. The liquid phase material may be injected to fill the cavity 218. The filler may conform to a shape of the crown of the mold 225. Thus, the object formed from the filler after curing may conform to a contour of a tooth crown of the patient. In one embodiment, a liner 230 is placed between the mold 225 and the cavity 218. The liner 230 may be a non-stick coating, a thin plastic or other liner that may be applied to the mold 225 prior to insertion of the mold 225 into the plastic shell 205. The liner 230 may prevent the filler from bonding to the mold 225.

Figure 2F:
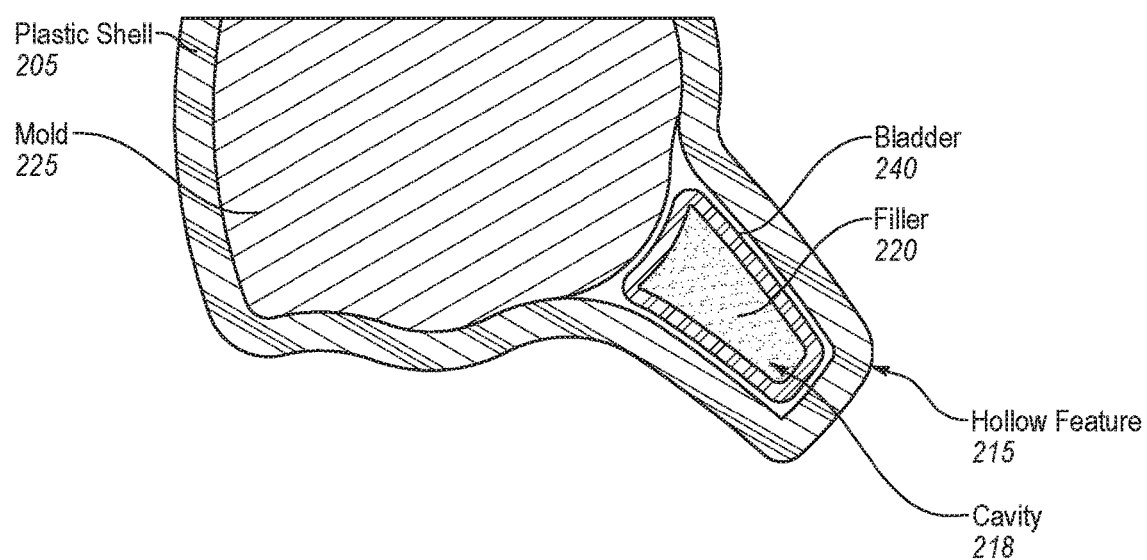
FIG. 2F illustrates a cross sectional side view of the plastic shell of FIG. 2B after the plastic shell has been placed over a second mold and a cavity in a hollow feature of the plastic shell has been filled by a filler, in accordance with one embodiment.

FIG. 2F illustrates a cross sectional side view of the plastic shell 205 of FIG. 2B after the plastic shell 205 has been placed over a second mold 225 and a cavity 218 in a hollow feature 215 of the plastic shell 205 has been filled by a filler 220, in accordance with one embodiment. In the embodiment shown in FIG. 2F an inflatable bladder 240 has been inserted into the cavity 218 prior to insertion of the mold 225 into the plastic shell 205. The filler 220 may be injected into the inflatable bladder 240, causing the inflatable bladder 240 to fill the cavity 218 and conform to a shape of the cavity 218 and of a tooth crown of the mold 225. The filler 220 may be injected through a hole similar to hole 235. By injecting the filler 220 into the bladder 240, the filler 220 may be prevented from leaking into regions outside of the cavity 218. Additionally, the bladder 240 may prevent the filler 220 from bonding to the mold 225. The inflatable bladder 240 may be a plastic, rubber, latex, vinyl, or other material.

For the embodiments discussed with reference to FIGS. 2A-2F, an inside of the cavity 218 may be coated with an adhesive prior to injecting filler 220 into the cavity 218. The adhesive may be a light curable adhesive (e.g., an epoxy that is cured using ultraviolet light), a heat activated adhesive, a time activated adhesive, or other type of adhesive. Alternatively, or additionally, a laser welding or ultrasonic welding process may be performed to bond or weld the object formed from the filler 220 to the plastic shell 205. For example, if the filler 220 is a two phase plastic, then the laser welding or ultrasonic welding may melt the object and the plastic shell 205 at an interface between the object and the plastic shell 205. Melted portions of the object and plastic shell 205 may re-harden in a bonded or fused state.

Figure 3A:
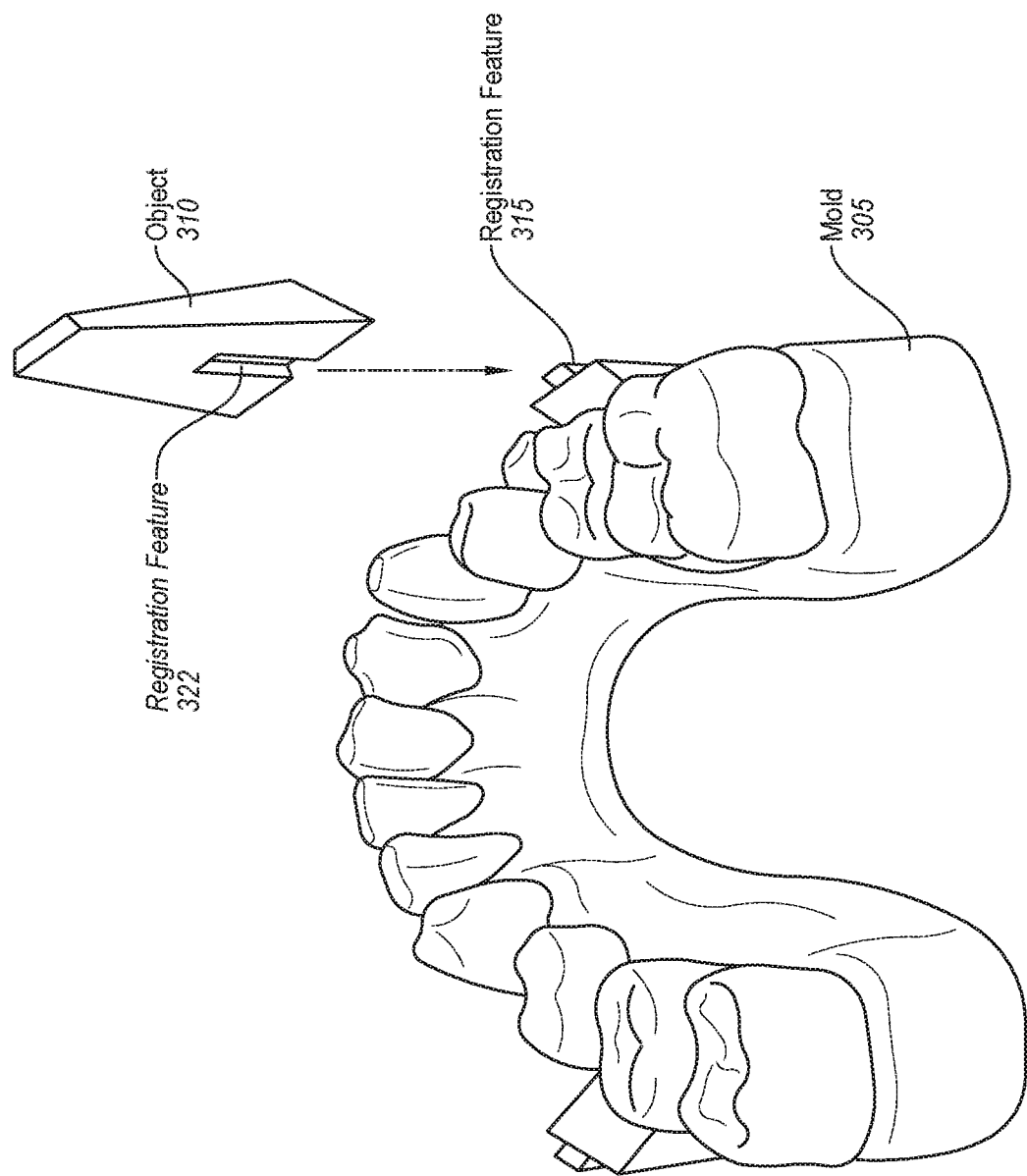
FIG. 3A illustrates a mold of a dental arch and an object that fits over the mold, in accordance with one embodiment.
Figure 3C:
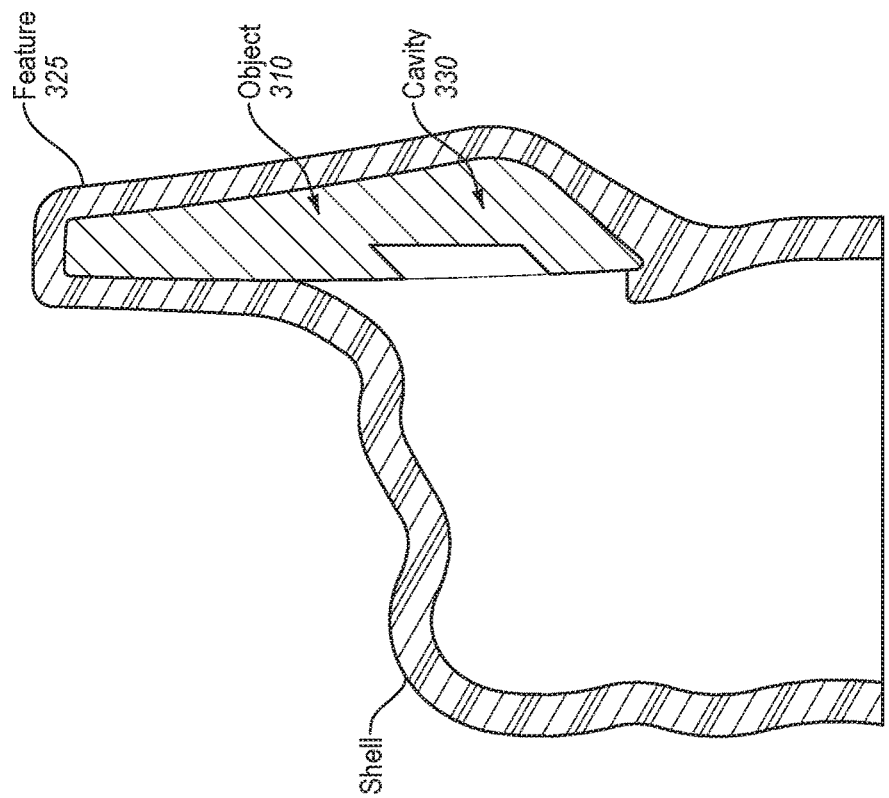
FIG. 3C illustrates a cross sectional side view of the plastic shell of FIG. 3B after it is has been removed from the mold, in accordance with one embodiment.
Figure 3B:
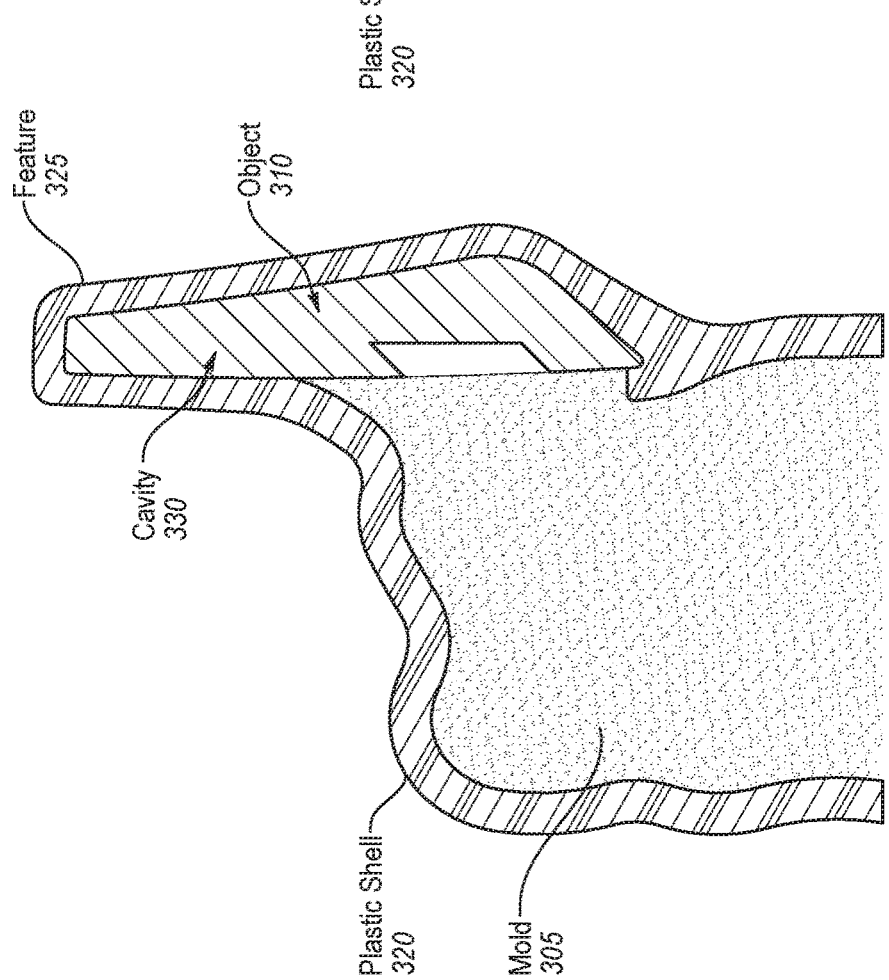
FIG. 3B illustrates a cross sectional side view of a plastic shell formed over the mold of FIG. 3A, in accordance with one embodiment.
Figure 4:
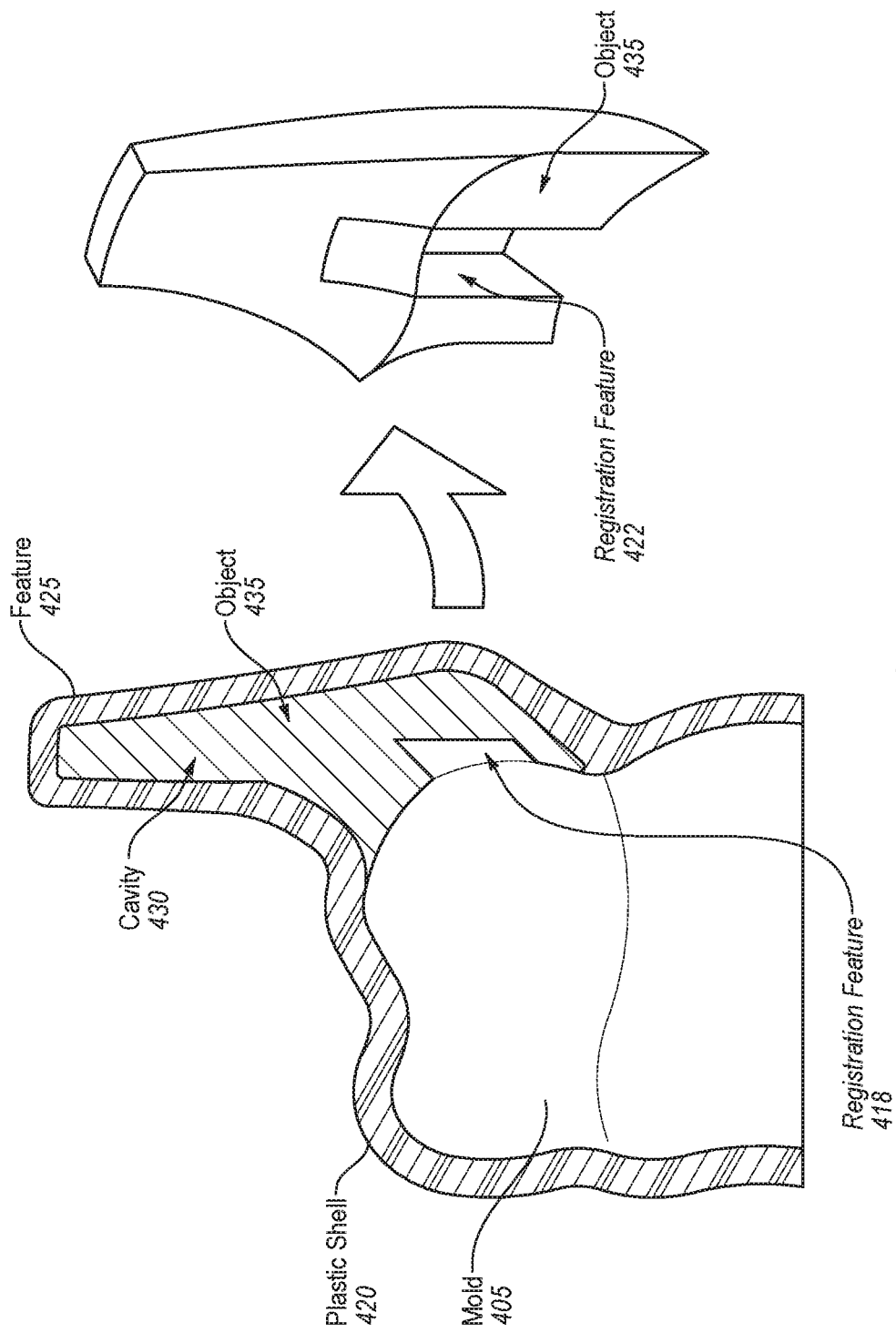
FIG. 4 illustrates a cross sectional side view of a plastic shell formed over a mold similar to the mold of FIG. 3A, in accordance with one embodiment.

FIGS. 3A-4 illustrate various embodiments of a plastic shell that is formed over an object and mold and that retains that object inside of a feature of the plastic shell when the plastic shell is removed from the mold. FIG. 3A illustrates a mold 305 of a dental arch and an object 310 that fits onto the mold 305, in accordance with one embodiment. In the illustrated embodiment the object 310 is a stock (also referred to as standard or universal) prefabricated object. The object 310 may be plastic, metal, ceramic, carbon fiber, or other materials. Patient customization may be satisfied using the stock object 310 by controlling the position and orientation of the object 310 and by selecting an appropriately sized and/or shaped prefabricated object 310. The object 310 may be selected from a selection of numerous prefabricated objects of varying shapes and sizes so as to form a feature in a plastic shell formed over the mold 305 and object 310 that will perform a particular desired function (e.g., to apply a desired force).

The mold 305 is a mold of a patient's dental arch (or a portion of the patient's dental arch). The mold 305 may be manufactured based on a digital model of the patient's dental arch (e.g., printed using rapid prototyping or three-dimensional (3D) printing) or based on an impression. The mold 305 includes one or more registration features 315. The registration features 315 may be added to the digital model prior to manufacturing the mold. The registration features 315 may be automatically selected and placed onto the digital model based on a treatment plan for the patient. Alternatively, the registration features 315 may be selected and placed into the digital model by a technician.

A registration feature 315 is used to register an object 310 to the mold and to retain that object 310 on the mold 305 during the formation of a plastic shell over the mold 305 and object 310. The object 310 may include an additional registration feature 322 that is shaped to mate with (e.g., to slide over and/or rest on) the registration feature 315. The size and shape of the registration feature 315 and/or registration feature 322 may be at least partially dependent on the size and shape of the object 310 to be placed on the registration feature 315. Examples of registration features 315, 322 include dovetail ways, grooves, projections, flat regions (e.g., landing pads), and so on.

FIG. 3B illustrates a cross sectional side view of a plastic shell 320 formed over the mold 305 of FIG. 3A, in accordance with one embodiment. As shown, the plastic shell 320 is formed over the mold 305 and over the object 310. The formation of the plastic shell 320 over the object 310 causes the plastic shell to have a feature 325. The feature 325 would be a hollow feature with a cavity 330 were the object 310 to be removed from the feature 325. Since the plastic shell is formed (e.g., thermoformed) over the object 310, the feature has a contour that matches a shape of the object 310.

FIG. 3C illustrates a cross sectional side view of the plastic shell 320 of FIG. 3B after the plastic shall 320 has been removed from the mold 305, in accordance with one embodiment. As shown, the feature 325 of the plastic shell 320 that is formed over the object 310 is shaped such that removal of the object 310 from the plastic shell 320 may be difficult or unobtainable. For example, the object 310 may be tapered in a manner that causes the plastic shell 320 to mechanically interlock with the object 310. The object 310 may additionally or alternatively include retentions features such as ridges, lips, knurling, tapering, etc. to mechanically interlock the object 310 with the plastic shell 320. The feature retains the object 310 inside of the cavity 330 in the feature 325 when the plastic shell 320 is removed from the mold 305. Thus, the object 310 may be a permanent part of the plastic shell 320.

FIG. 4 illustrates a cross sectional side view of a plastic shell 420 formed over a mold 405 similar to the mold 305 of FIG. 3A, in accordance with one embodiment. As shown, the mold 405 includes a registration feature 418. A custom shaped object 435 having another registration feature 422 is attached to the mold 405 by mating the registration feature 418 of the mold with the registration feature 422 of the object 435. Alternatively, registration features may not be used. A plastic shell 420 is formed over the mold 405 and custom shaped object 435. When the plastic shell 420 is removed from the mold 405, the object 435 may be retained inside of a cavity 430 in a feature 425 of the plastic shell 420.

The object 435 may have one or more custom faces 440 or sides that are shaped to conform to a unique shape of a patient's tooth. Thus, the object 435 may have a size and/or shape that are determined for use on the patient. The custom shaped object 435 may be manufactured by generating a 3D model of the custom shaped object and then using a 3D printing or rapid prototyping process to print the custom shaped object 435. In one embodiment, a technician selects a stock object and a location on a 3D model of a patient's dental arch where the object is to be placed. Processing logic may then determine contours for one or more faces of the stock object to convert the stock object into a custom object. Alternatively, the custom shaped object 435 may be manually sculpted onto the mold 405. For example, a mold for the object may be filled with a pliable material and then pressed against the mold 405 to manually sculpt one or more faces of the custom shaped object 435.

The embodiments discussed with reference to FIGS. 3A-4 have objects that are separate from a mold that the objects are then attached to. Additionally or alternatively an object may be a feature of a mold that has a breakable region. The breakable region may break when the plastic shell is removed from the mold, and the object may be retained inside of the plastic shell. Thus, a portion of the mold 305 may separate from a remainder of the mold and may be permanently retained inside of the plastic shell.

For the embodiments discussed with reference to FIGS. 3A-4, the object 310, 435 may be coated with an adhesive prior to forming the plastic shell 320, 420 over the object 310, 435. Alternatively, or additionally, a laser welding or ultrasonic welding process may be performed to bond or weld the object 310, 435 to the plastic shell 320, 420. For example, if the object 310, 435 is a plastic, then the laser welding or ultrasonic welding may melt the object 310, 435 and the plastic shell 320, 420 at an interface between the object and the plastic shell. Melted portions of the object and plastic shell may re-harden in a bonded state.

Figure 5B:
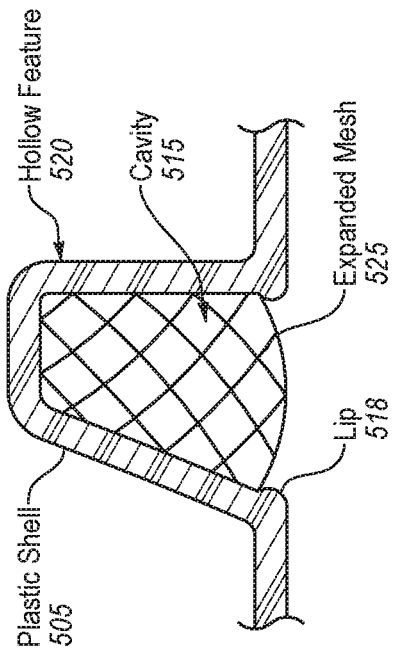
FIG. 5B illustrates a cross sectional side view of an mesh being in the cavity of the plastic shell of FIG. 5A, in accordance with one embodiment.
Figure 5A:
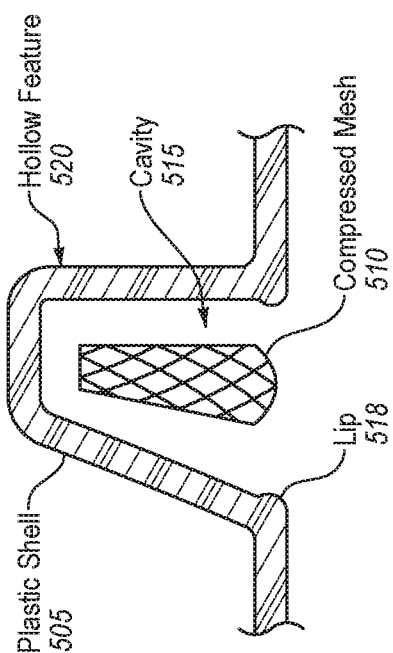
FIG. 5A illustrates a cross sectional side view of compressed mesh being placed into a cavity of a plastic shell, in accordance with one embodiment.

FIG. 5A illustrates a cross sectional side view of compressed mesh 510 being placed into a cavity 515 of a plastic shell 505, in accordance with one embodiment. The plastic shell 505 has a hollow feature 520 that may have been formed in a similar manner as described with reference to FIGS. 2A-2B. However rather than filling the cavity 515 in the hollow feature 520 with a curable liquid material, the compressed mesh 510 may be inserted into the cavity 515. The compressed mesh 510 may be compressed, for example, by a retaining sleeve.

FIG. 5B illustrates a cross sectional side view of an expanded mesh 525 in the cavity 515 of the plastic shell 505 of FIG. 5A, in accordance with one embodiment. The compressed mesh 510 may be spring-loaded and under force to expand. After the compressed mesh 510 has been inserted into the cavity 515, the mesh may expand into expanded mesh 525. If a retaining sleeve is used to compress the mesh, then the retaining sleeve may be removed after the mesh is inserted into the cavity 515 to enable the mesh to expand. The cavity 515 may be shaped to have a taper or other retention feature that will retain the expanded mesh 525 inside of the cavity 515. In one embodiment, the cavity 515 has a lip or ledge 518 that retains the expanded mesh 525 within the cavity 515.

Figure 6A:
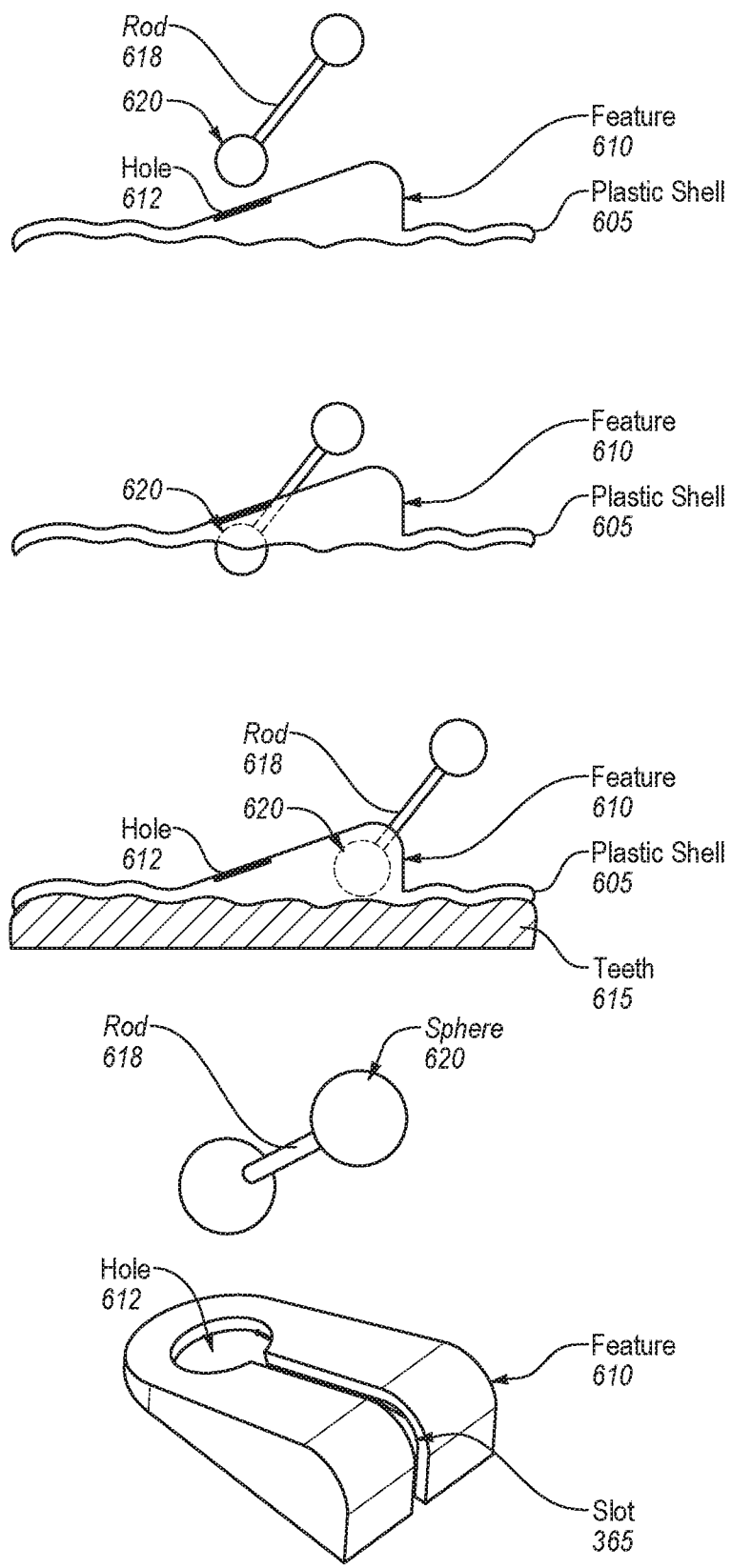
FIG. 6A illustrates cross sectional views of a ball inserted into a feature of a plastic shell, in accordance with one embodiment.

FIG. 6A illustrates cross sectional views of a sphere 620 at an end of a rod 618 inserted into a feature 610 of a plastic shell 605, in accordance with one embodiment. The feature 610 may be a hollow feature in some embodiments. The feature 610 may include a hole 612 and a slot 635. The hole 612 may be sized to enable the sphere 620 to fit into the hole 612 and may be positioned at a first side of the feature 610. For example, the hole 612 may have the same diameter or a slightly larger diameter than a diameter of the sphere. The slot 635 may have a width that is approximately equal to a thickness of the rod 618. The slot 635 may extend from the hole 612 to a second end of the feature 610.

The sphere 620 can be inserted into the hole 612 at the first end of the feature 610, and then the rod 618 and attached sphere 620 be moved to the second end of the feature 610. While the rod 618 and sphere 620 are at the second end of the feature 610, the sphere 620 is retained within the feature 610.

The feature 610 may be formed in the plastic shell 610 according to any of the aforementioned techniques for forming a plastic shell having a hollow feature. The hole 612 and slot 635 may then be cut into the feature after the plastic shell 605 is formed.

In one embodiment, an object (not shown) is inserted into the feature 610 as previously described above. The object may be a prefabricated object that includes a hole and slot that may substantially match the hole 612 and slot 635. By cutting the hole 612 and slot 635 into the feature 610 of the plastic shell 605, access may be gained to the corresponding hole and slot in the object. Alternatively, the plastic shell 610 may be thermoformed over an object having deep recessions and a concave geometry to cause feature 610 to be created with the hole 612 and slot 635. For example, the object may have a hole and slot, and by thermoforming the plastic shell 610 over the object, the plastic shell 610 may form the feature 610 also having the hole 612 and slot 635.

In one embodiment, the feature 610 is tapered such that the second end has a greater height than the first end that includes the hole 612. The sphere 620 may be inserted into the feature 610 prior to the plastic shell 605 being worn by a patient. Once the plastic shell 605 with the inserted sphere 620 is placed on the patient's dental arch, the patient's teeth 615 may physically prevent the sphere 620 and attached rod 618 from being removed from the plastic shell 605.

Figure 6B:
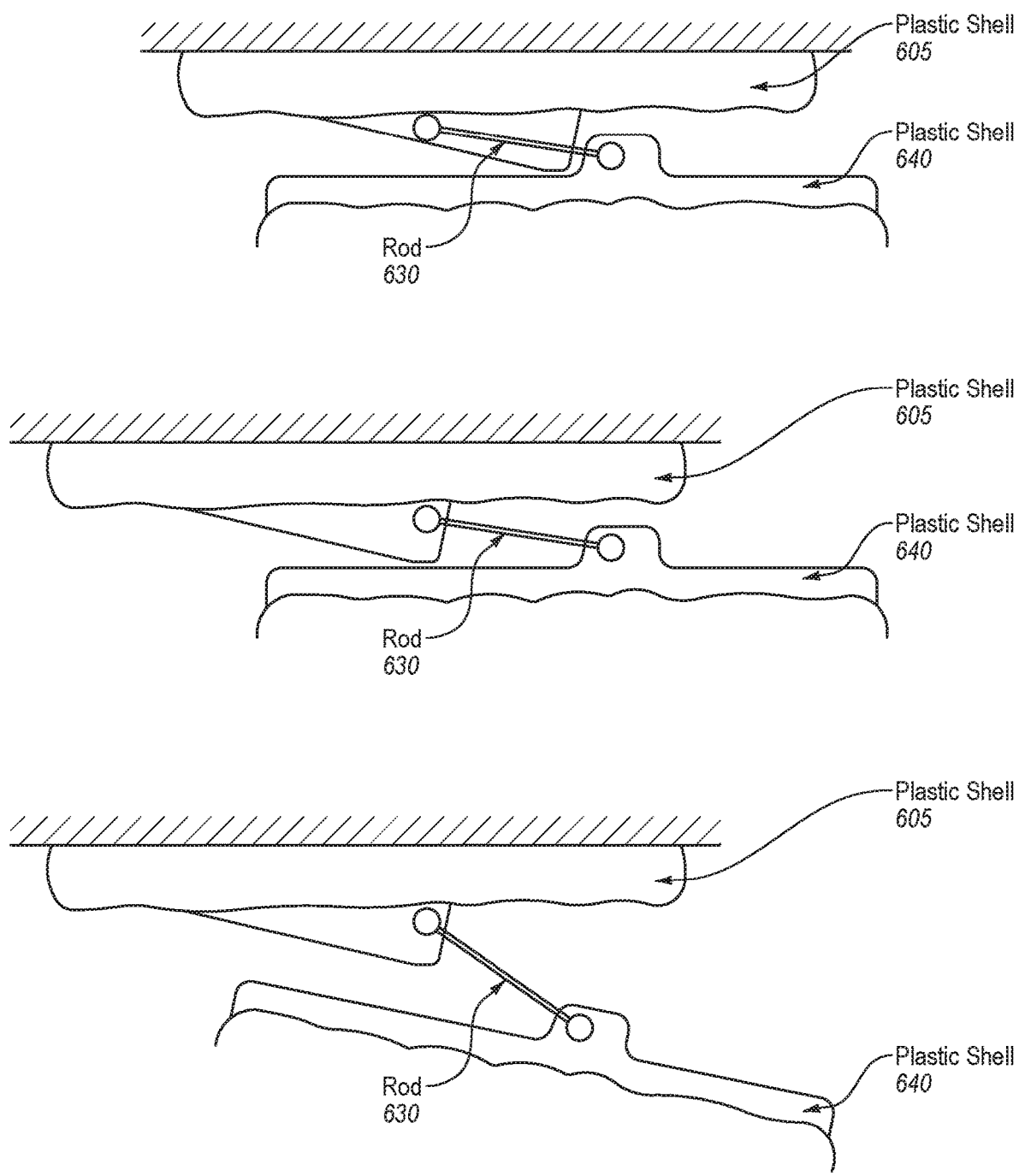
FIG. 6B illustrates cross sectional views of a ball ended rod into a feature of a plastic shell, in accordance with one embodiment.

FIG. 6B illustrates cross sectional views of a rod 630 with attached spheres inserted into features of two plastic shells 605, 640, in accordance with one embodiment. Plastic shell 605 may be placed over a patient's upper teeth and plastic shell 640 may be placed over the patient's lower teeth after the spheres at the ends of the rod have been respectively inserted into the plastic shells 605, 640. In the illustrated example, the patient's upper jaw may be fixed, while the patient's lower jaw may be free to open and advance but not free to retract. Thus, the rod 630 may act as a linkage between plastic shell 605 and plastic shell 640, and may restrict the articulation or motion of the patient's jaw.

Though FIGS. 6A-6B describe the insertion of spheres at the end of rods into holes and/or slots in the plastic shells, at least portions of other types of objects may also be inserted into slots and/or holes in the plastic shells. The slots or holes may be generally used as registration features for insertion of objects. Such objects may have a structure or feature that mates with the hole and/or slot that is cut into the shell. A ball ended rod as described above is one type of joint that may be implemented. The ball ended rod is one example of a three degree of freedom hinge joint. Other 1 degree of freedom or 2 degree of freedom hinge joints may also be implemented. Other types of joints to control articulation of the jaw may also be implemented. For example, the feature 610 may be or include a housing or socket for other joints such as a sliding joint, a hinge joint, a friction fit joint, a dovetail joint, a flexural joint, and so on. For a sliding joint, the object may include a track instead of a hole and/or slot that act as a ball socket. A 1 degree of freedom sliding joint would allow for protrusive-retrusive motions while constraining jaw opening. The joints may be dynamic joints or static joints. Static joints may be configured to receive a supplementary or replaceable feature onto the aligner. Such supplementary or replaceable features may be mandibular advancement or jaw positioning features, compliance indicators, or other features.

Figure 7A:
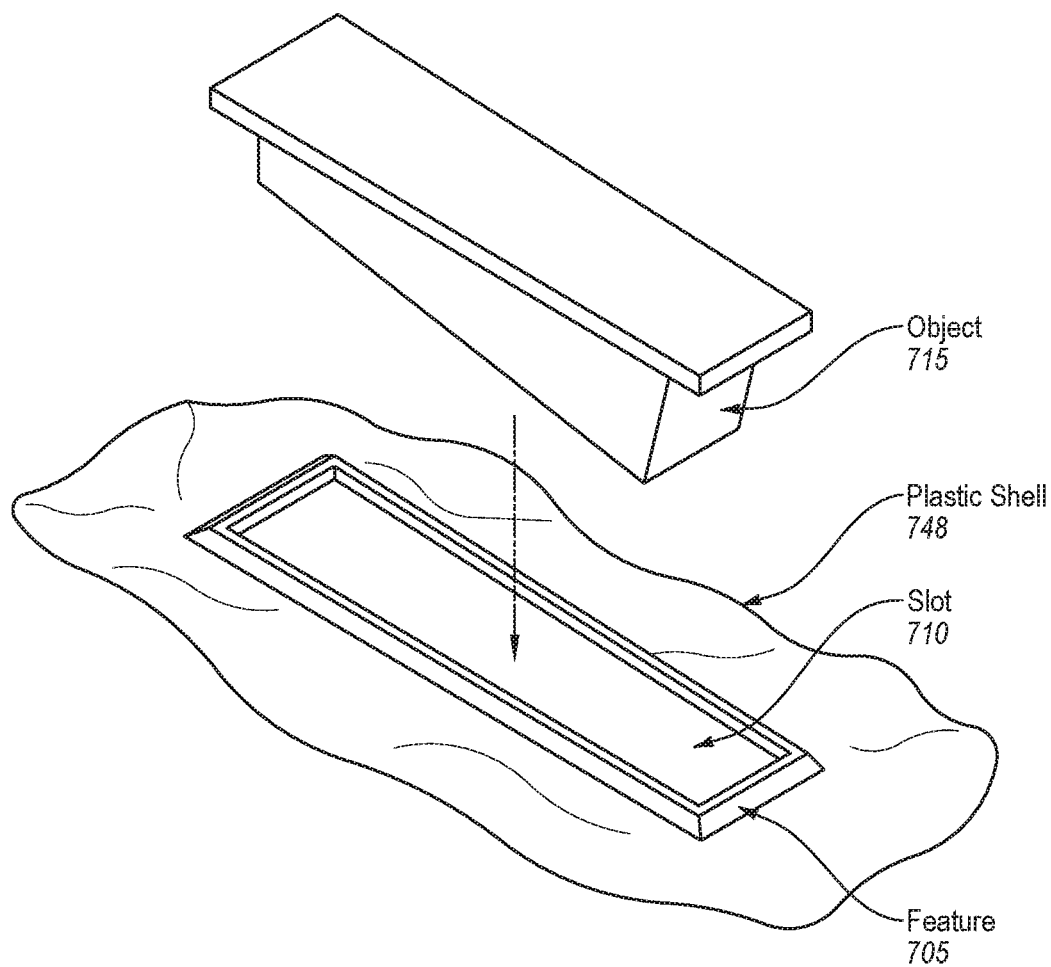
FIG. 7A illustrates views of an object inserted into a feature of a plastic shell, in accordance with one embodiment.
Figure 7A:
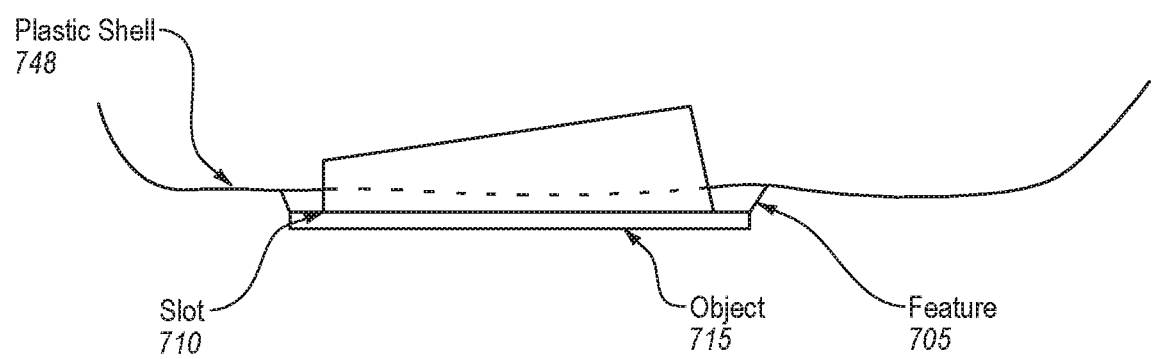

FIG. 7A illustrates views of an object 715 inserted into a feature 705 of a plastic shell 748, in accordance with one embodiment. The feature 705 may be formed using any of the techniques as discussed above. After the plastic shell 748 having the feature 705 is formed, a slot 710 is cut into the feature, such as by laser cutting or mechanical cutting. An object 715 may then be inserted into the feature 705 through the slot. The object may have a particular height and/or shape to perform a desired function with regards to a patient's mouth, jaw and/or teeth. In the illustrated example the object 715 is a shim usable to open a patient's bite. The object 715 may be removable from the feature 705, and another object (not shown) having a different size and/or shape may be inserted into the slot 710. Thus, a single plastic shell 748 may be used to perform, for example, multiple different adjustments which traditionally might require multiple different plastic shells.

Figure 7B:
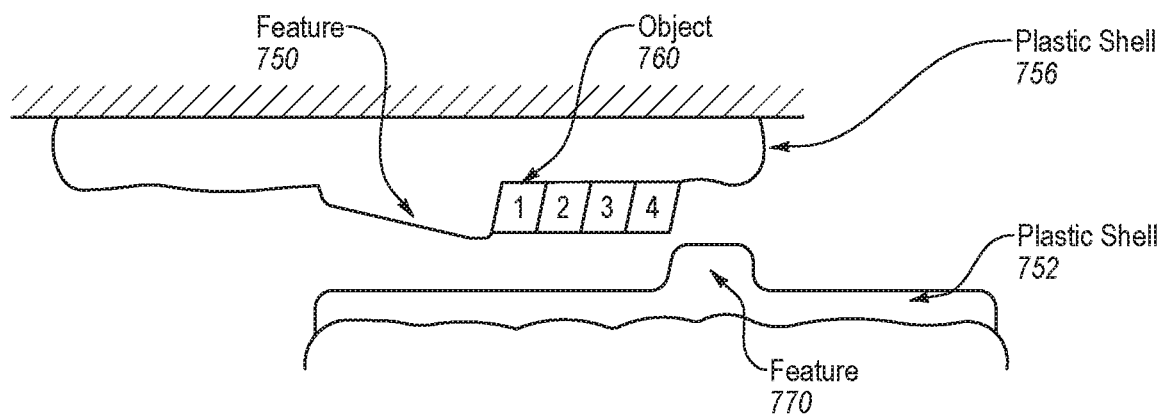
FIG. 7B illustrates a cross sectional view of an object inserted into a feature of a plastic shell, in accordance with one embodiment.

FIG. 7B illustrates a cross sectional view of multiple objects inserted into a feature 750 of a plastic shell 756, in accordance with one embodiment. In the illustrated example, the objects 760 line up with a feature 770 in another plastic shell 752. For example, plastic shell 756 may be for an upper arch of a patient and plastic shell 752 may be for a lower arch of the patient. The objects 760 and feature 770 may control a resting bite position of a patient's jaw, for example. The plastic shell with the objects 760 may be used, for example, for jaw repositioning of a patient.

Figure 7C:
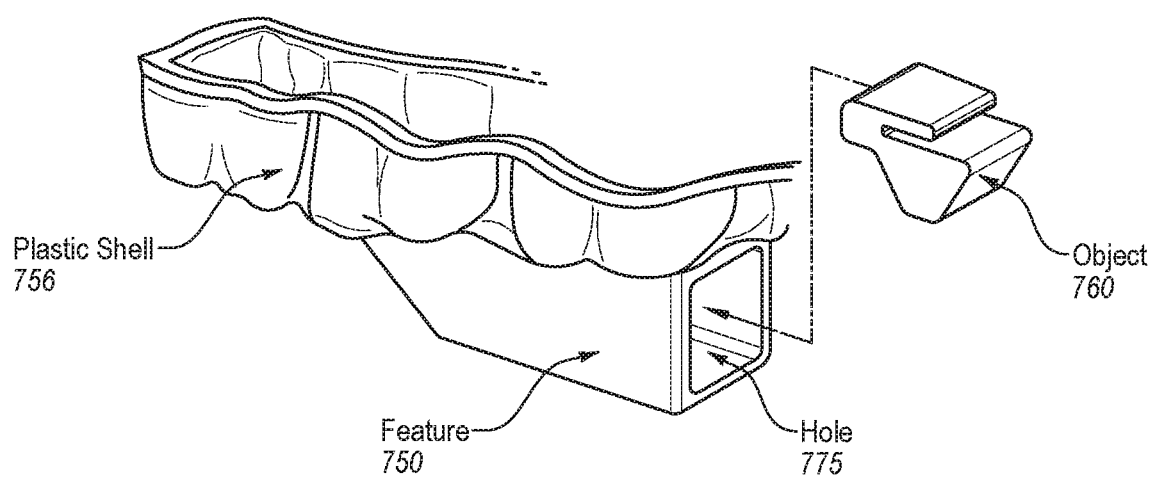
FIG. 7C illustrates a perspective view of the object inserted into the feature of the plastic shell of FIG. 7B, in accordance with one embodiment.

FIG. 7C illustrates a perspective view of one of the objects 760 inserted into the feature 750 of the plastic shell 756 of FIG. 7B, in accordance with one embodiment. The feature 750 may be formed using any of the techniques as discussed above. After the plastic shell 756 having the feature 750 is formed, a hole 755 is cut into the feature such as by laser cutting or mechanical cutting. An object 760 may then be inserted into the feature 750 through the hole. The object 760 may clip onto or otherwise mechanically interlock with the feature 750. The object 760 may have a particular length and/or shape to perform a desired function with regards to a patient's mouth, jaw and/or teeth. The object 760 may be removable from the feature 750, and another object having a different size and/or shape may be inserted into the hole 755. Alternatively, or additionally, multiple objects 760 may be inserted into and/or attached to the feature 750 (e.g., as shown in FIG. 7B). In one embodiment, one or more of the objects 760 are shaped to enable them to interlock with one another. A portion of the object or objects 760 may stick out of the feature 750 in some embodiments. Thus, a single plastic shell 756 may be used to perform, for example, multiple different adjustments which traditionally might require multiple different plastic shells.

In some embodiments the objects described with reference to FIGS. 7A-7C may be attached to the plastic shells at some times and removed from the plastic shells at other times. For example, a patient may attach the objects to the plastic shells during the night (e.g., before the patient goes to sleep) and remove the objects from the plastic shells during the day (e.g., after the patient wakes up in the morning).

The orthodontic aligners (and other plastic shells) described herein can be used in combination with one or more attachments mounted onto one or more of the teeth over which the plastic shells are placed. Accordingly, the topography of the plastic shells can be modified to accommodate the attachment (e.g., with a suitable receptacle for receiving the attachment). The attachment can engage the plastic shells and/or elastics to transmit repositioning forces to the underlying teeth. Alternatively or in addition, the attachment can be used to retain the plastic shell on the patient's teeth and prevent it from inadvertently becoming dislodged. For example, teeth with no undercuts (e.g., central teeth, lateral teeth) may benefit from an attachment to ensure correct engagement of the plastic shell onto the teeth, while teeth with natural undercuts (e.g., molars) may not benefit from an attachment. The attachment can be mounted onto any suitable portion of the tooth, such as on a buccal or lingual surface of the tooth.

FIGS. 8A-8D illustrate plastic shells (e.g., orthodontic aligners) having features that alter contact points between an upper and lower dental arch of a patient. These plastic shells may be used for bite stabilization (e.g., flat plane stabilization for temporomandibular joint disorder (TMD), to address asymmetric contact between teeth of a patient's upper and lower dental arch, etc.), to increase bite separation, to reposition the jaw, to alter occlusal contacts, and so on. These plastic shells may add substantial volume in an inter-arch space between an upper dental arch and a lower dental arch of a patient, which can make manufacturing of these plastic shells challenging.

Figure 8A:
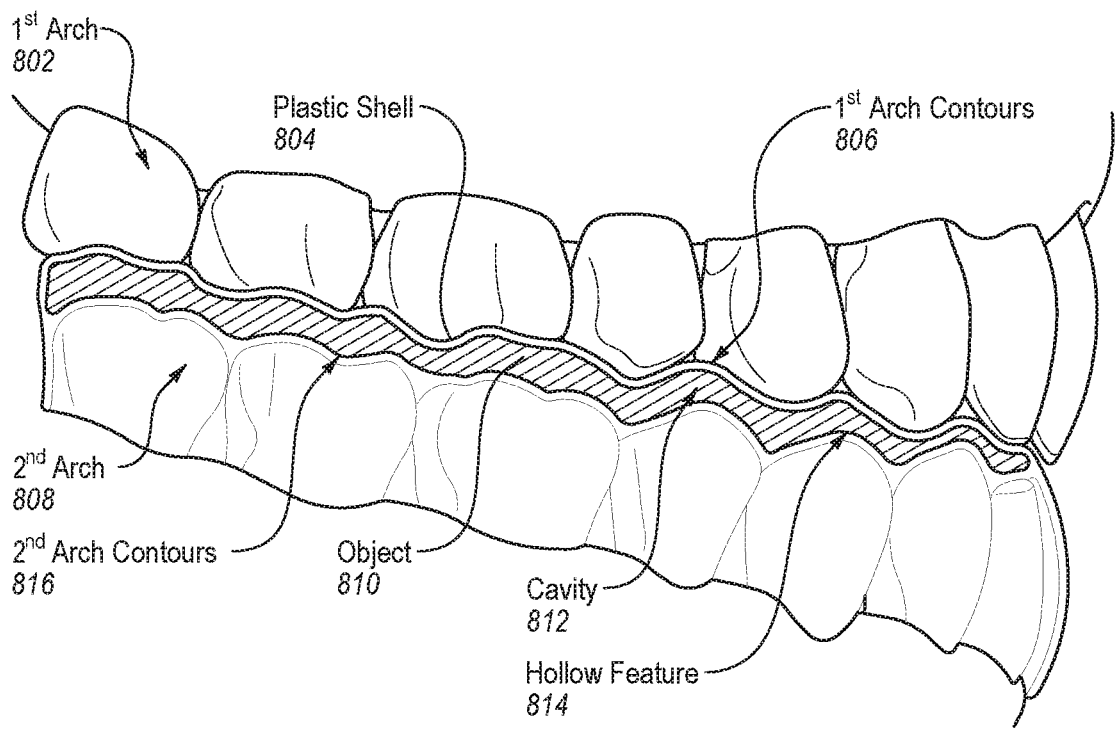
FIG. 8A illustrates a cross sectional side view of a plastic shell on a dental arch, in accordance with one embodiment.

FIG. 8A illustrates a cross sectional side view of a plastic shell 804 on a dental arch (second dental arch 808), in accordance with one embodiment. As shown, the plastic shell 804 is being worn on second dental arch 808 (the lower dental arch) and has an outer surface that conforms to the contours 806 of at least some teeth in the first dental arch 802 (the upper dental arch). An interior of the plastic shell 804 additionally conforms to the contours 816 of the teeth in the second dental arch 816. The plastic shell 804 may provide equal contact points for all teeth in the first dental arch 802 and/or the second dental arch 808. Such a plastic shell 804 may be used, for example, for TMD splints and/or anterior deprogrammers.

To enable the plastic shell 804 to conform both to the contours of the first arch 802 and the second arch 808, first mold (not shown) may first be generated of the second arch 808. In one embodiment, rather than the first mold having contours that match the contours of the teeth in the second arch, the first mold may have contours that correspond to the contours of the first arch 802 (the opposing arch). The first mold may have contours that conform to a negative or inverse of the first arch 802 in one embodiment. The plastic shell 804 may be thermoformed over the first mold to cause an outer surface of the plastic shell 804 to match the contours 806 of the first arch 802.

The plastic shell 804 may have a hollow feature 814 with a cavity 812. The cavity 812 may be empty space between the teeth on the second arch 808 and the inner surface of the plastic shell 804 when the plastic shell 804 is worn. An object 810 may be inserted into the cavity 812 to fill the empty space. The object 810 may have a first surface with a shape that matches contours of the walls of the cavity 812. The object 810 may additionally have an opposing second surface with a shape that matches the contours of the teeth in the second arch 808.

In one embodiment, the object 810 is a preformed object that is shaped to fit into the cavity 812. Alternatively, the object 810 may be formed from a two phase material that is injected into the cavity 812 in a liquid phase and that is subsequently cured to transform into a solid phase. In such an embodiment, the plastic shell 804 may be placed onto a second mold (not shown) of the second arch 808. The two phase material may then be injected into the cavity through a hold in the plastic shell 804 and then cured. Alternatively, the two phase material may be injected into the cavity through a hole in the second mold.

In one embodiment, the first mold includes registration features for receiving the object 810, and the object 810 is placed onto the first mold using the registration features. The plastic shell 804 may then be thermoformed over the first mold and the object 810, and the object may be retained inside of the plastic shell 804.

Any of the techniques and/or options discussed with reference to FIGS. 1A-4 may be used to manufacture the plastic shell 810 in embodiments.

Figure 8B:
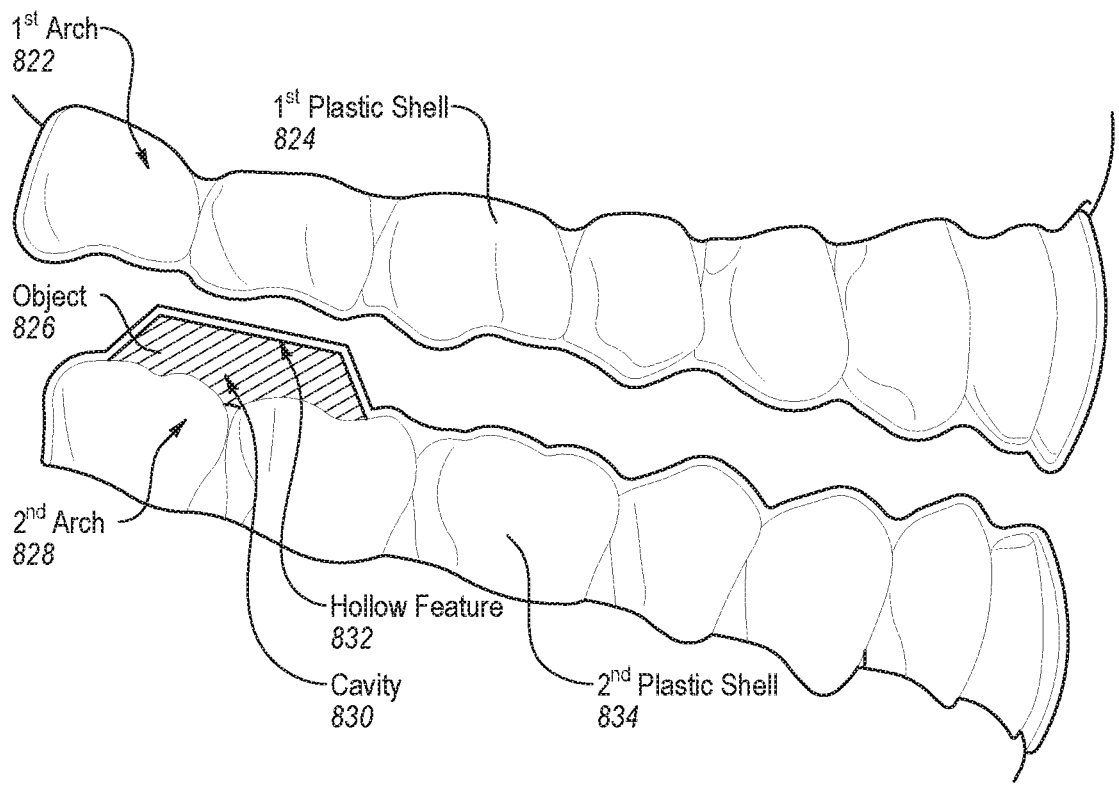
FIG. 8B illustrates a cross sectional side view of pair of plastic shells on upper and lower dental arches, in accordance with one embodiment.

FIG. 8B illustrates a cross sectional side view of pair of plastic shells on upper and lower arches of a patient, in accordance with one embodiment. In FIG. 8B a first plastic shell 824 is disposed on a first arch 822 (e.g., an upper arch). A second plastic shell 834 is disposed on a second arch 828 (e.g., a lower arch). The second plastic shell 834 includes a hollow feature 832 having a cavity 830. The hollow feature 832 may be, for example, a bite ramp or an anterior guidance feature. The cavity 830 is filled with an object 826. The second plastic shell 834 may be manufactured using any of the techniques described herein.

Figure 8C:
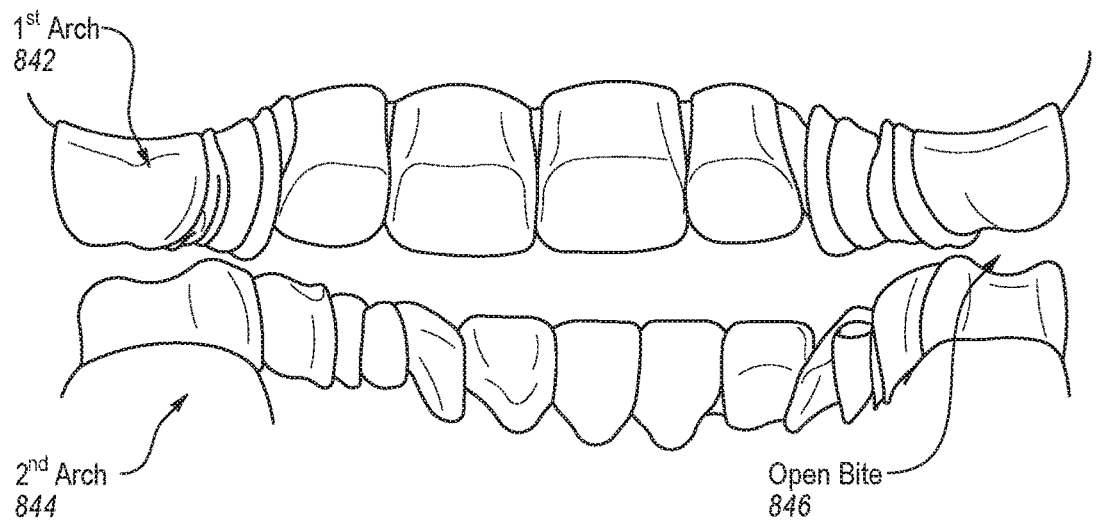
FIG. 8C illustrates a back view of an upper and lower dental arch, in accordance with one embodiment.

FIG. 8C illustrates a back view of an upper and lower dental arch of a patient, in accordance with one embodiment. As shown, when the patient bites, a left side of a first dental arch 842 of the patient and a second dental arch 844 of the patient close. However, a right side of the first dental arch 842 and the second dental arch 844 of the patient do not close, causing an open bit 846 on the right side.

Figure 8D:
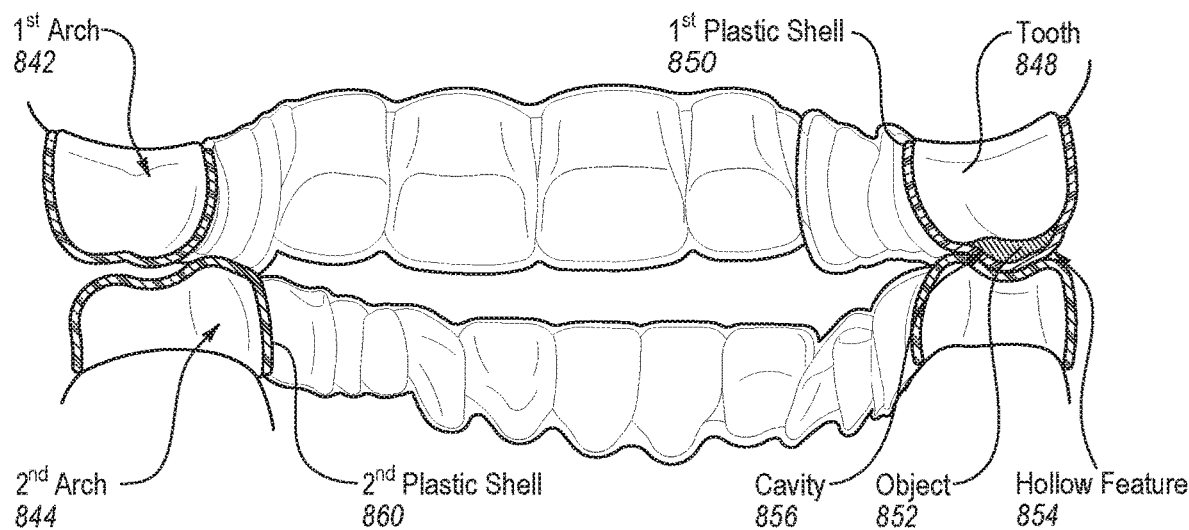
FIG. 8D illustrates a back view of plastic shells on the upper and lower dental arches of FIG. 8C, in accordance with one embodiment.

FIG. 8D illustrates a back view of plastic shells on the upper and lower dental arches of FIG. 8C, in accordance with one embodiment. As shown, the first dental arch 842 includes a first plastic shell 850 having a hollow feature 854 that bridges a gap between the first dental arch 842 and the second dental arch 844 at tooth 848 when the patient bites. The hollow feature 854 eliminates the open bite 846 and balances contact points between the upper and lower arches in posterior teeth while the first plastic shell 850 is worn. The hollow feature 854 includes a cavity 856 that is filled with an object 852. The first plastic shell 850 may be manufactured using any of the techniques described herein. As shown, a second plastic shell 860 may additionally be worn over the second dental arch 844.

Figure 9:
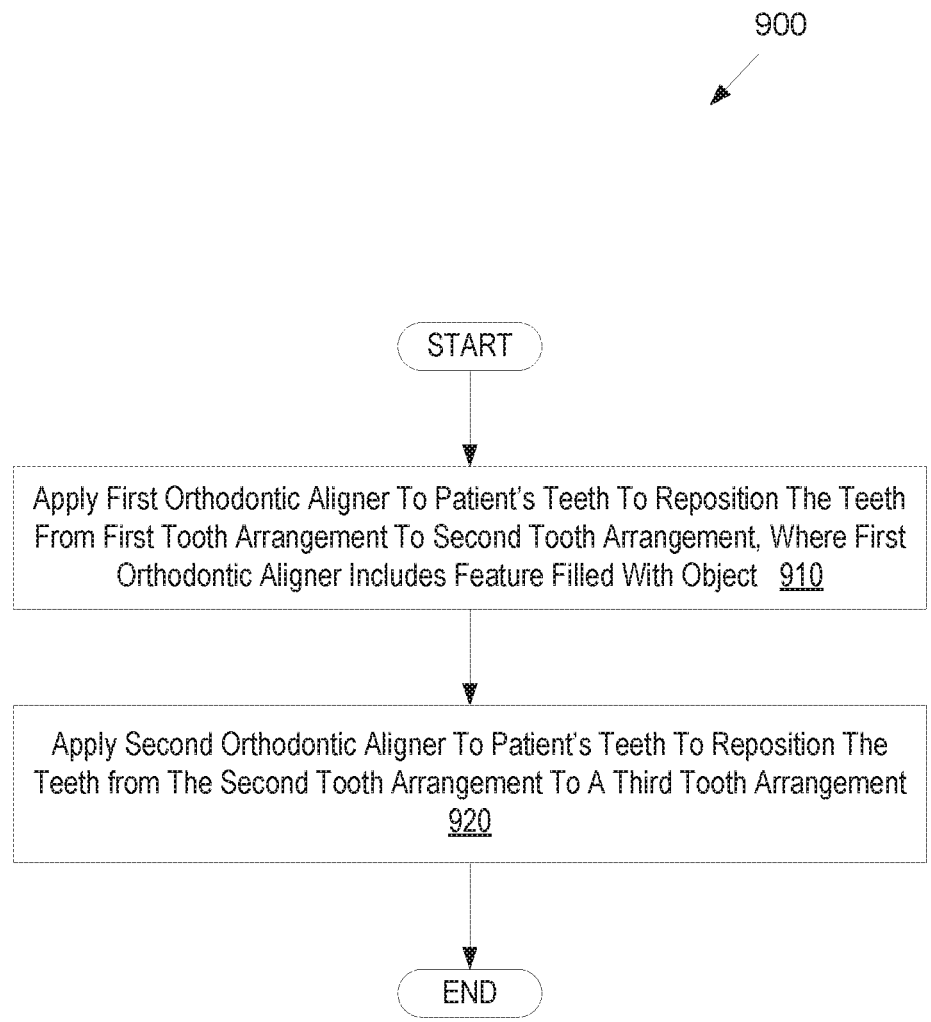
FIG. 9 illustrates a flow diagram of one embodiment for a method of orthodontic treatment using a sequence of aligners.

FIG. 9 illustrates a flow diagram of one embodiment for a method 900 of orthodontic treatment using a sequence of orthodontic aligners. The method 900 can be practiced using any of the orthodontic aligners or aligner sets described herein. In block 910, a first orthodontic aligner is applied to a patient's teeth in order to reposition the teeth from a first tooth arrangement toward a second tooth arrangement. The first orthodontic aligner may include a hollow feature that is at least partially filled by an object, as described herein above.

At block 920, a second orthodontic aligner is applied to the patient's teeth in order to reposition the teeth from the second tooth arrangement to a third tooth arrangement. The repositioning of the teeth from the second arrangement to the third arrangement may be accomplished using an additional orthodontic aligner or set of aligners. The additional orthodontic aligner or set of aligners may additionally include a hollow feature that is at least partially filled by an object, as described above. Alternatively, the second orthodontic aligner may be a standard orthodontic aligner without a hollow feature that includes an inserted or retained object. Accordingly, a traditional orthodontic aligner may be used to reposition the teeth from the second arrangement to the third arrangement.

The method 900 can be repeated using any suitable number and combination of sequential orthodontic aligners in order to incrementally reposition the patient's teeth from an initial arrangement to a target arrangement. The orthodontic aligners can be generated all at the same stage or in sets or batches (e.g., at the beginning of a stage of the treatment), and the patient can wear each orthodontic aligner until the pressure of each orthodontic aligner on the teeth can no longer be felt or until the maximum amount of expressed tooth movement for that given stage has been achieved. Multiple different orthodontic aligners (e.g., a set) can be designed and even fabricated prior to the patient wearing any orthodontic aligner. After wearing an orthodontic aligner for an appropriate period of time, the patient can replace the current orthodontic aligner with the next orthodontic aligner in the series until no more orthodontic aligners remain. The orthodontic aligners are generally not affixed to the teeth and the patient may place and replace the orthodontic aligners at any time during the procedure (e.g., patient-removable orthodontic aligners).

The final orthodontic aligner or several orthodontic aligners in the series may have a geometry or geometries selected to overcorrect the tooth arrangement. For instance, one or more orthodontic aligners may have a geometry that would (if fully achieved) move individual teeth beyond the tooth arrangement that has been selected as the "final." Such over-correction may be desirable in order to offset potential relapse after the repositioning method has been terminated (e.g., permit movement of individual teeth back toward their pre-corrected positions). Over-correction may also be beneficial to speed the rate of correction (e.g., an orthodontic aligner with a geometry that is positioned beyond a desired intermediate or final position may shift the individual teeth toward the position at a greater rate). In such cases, the use of an orthodontic aligner can be terminated before the teeth reach the positions defined by the orthodontic aligner. Furthermore, over-correction may be deliberately applied in order to compensate for any inaccuracies or limitations of the orthodontic aligner.

Figure 10:
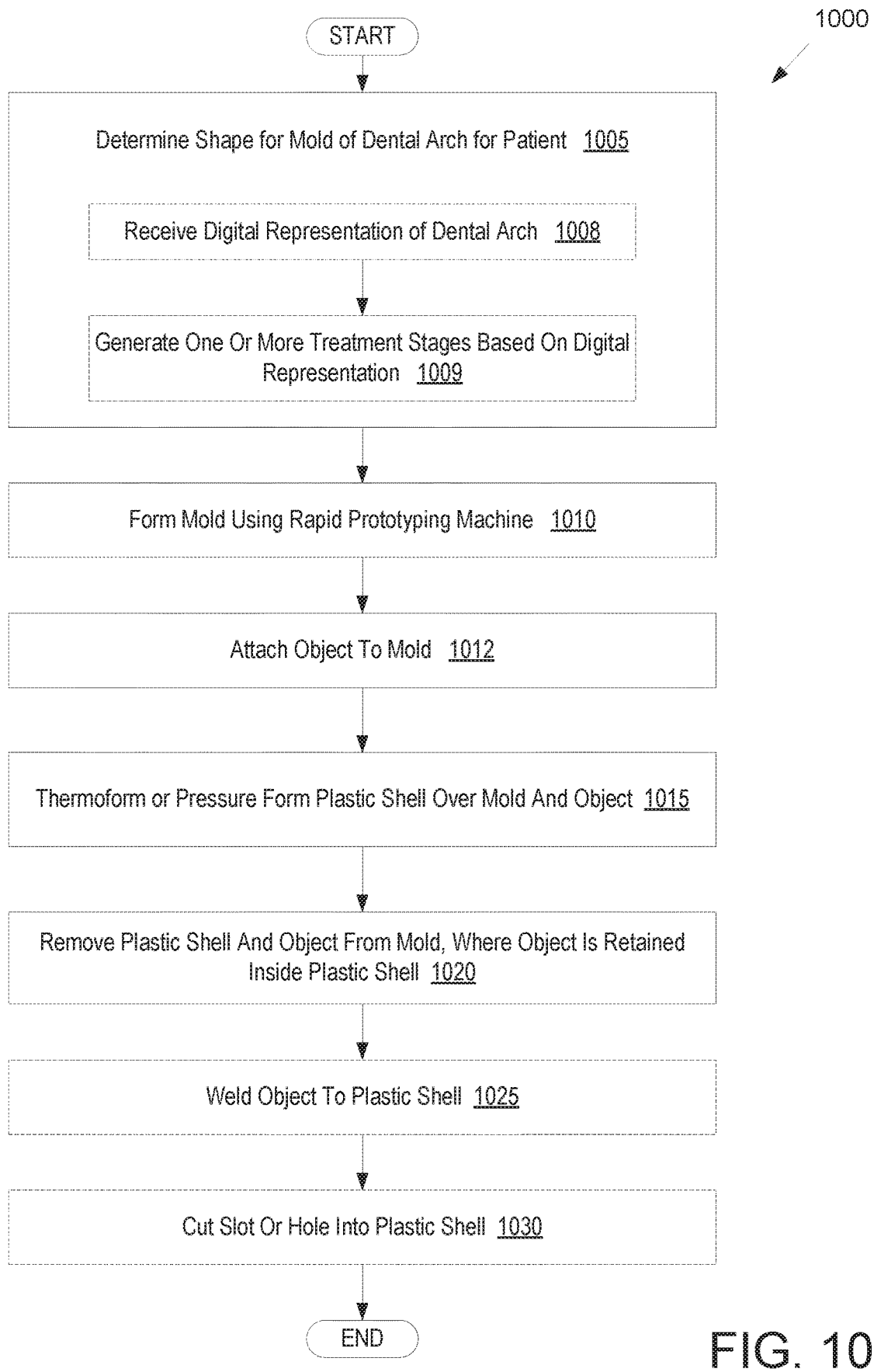
FIG. 10 illustrates a flow diagram of one embodiment for a method of manufacturing plastic shell having hollow feature that is at least partially filled by an object.

FIG. 10 illustrates a flow diagram of one embodiment for a method 1000 of manufacturing a plastic shell having a hollow feature that is at least partially filled by an object. In some embodiments, one or more operations of method 1000 are performed by processing logic of a computing device. The processing logic may include hardware (e.g., circuitry, dedicated logic, programmable logic, microcode, etc.), software (e.g., instructions executed by a processing device), firmware, or a combination thereof. For example, one or more operations of method 1000 may be performed by a computing device such as computing device 1301 of FIG. 13. Additionally, some operations may be performed by a fabrication machine based on instructions received from processing logic. Some operations may alternately be performed by a user.

At block 1005 of method 1000, a shape is determined for a mold of a dental arch for a patient. The shape may be determined by digitally planning a current, intermediate or final target arrangement of the patient's teeth, and fabricating a mold of a dental arch that reflects that target arrangement. Alternatively, the shape may be determined by taking an impression of a patient's arch and generating a mold from the impression. Thus, the mold or model can be generated from dental impressions or scanning (e.g., of the patient's intraoral cavity, of a positive or negative model of the patient's intraoral cavity, or of a dental impression formed from the patient's intraoral cavity).

Plastic shell fabrication or design can make use of one or more physical or digital representations of the patient's teeth. Representations of the patient's teeth can include representations of the patient's teeth in a current arrangement, and may further include representations of the patient's teeth repositioned in one or more treatment stages. Treatment stages can include a desired or target arrangement of the patient's teeth, such as a desired final arrangement of teeth. Treatment stages can also include one or more intermediate arrangements of teeth (e.g., planned intermediate arrangements) representing arrangements of the patient's teeth as the teeth progress from a first arrangement (e.g., initial arrangement) toward a second or desired arrangement (e.g., desired final arrangement).

In one embodiment, at block 1008 a digital representation of a patient's teeth is received. The digital representation can include surface topography data for the patient's intraoral cavity (including teeth, gingival tissues, etc.). The surface topography data can be generated by directly scanning the intraoral cavity, a physical model (positive or negative) of the intraoral cavity, or an impression of the intraoral cavity, using a suitable scanning device (e.g., a handheld scanner, desktop scanner, etc.).

In one embodiment, at block 1009 one or more treatment stages are generated based on the digital representation of the teeth. The treatment stages can be incremental repositioning stages of an orthodontic treatment procedure designed to move one or more of the patient's teeth from an initial tooth arrangement to a target arrangement. For example, the treatment stages can be generated by determining the initial tooth arrangement indicated by the digital representation, determining a target tooth arrangement, and determining movement paths of one or more teeth in the initial arrangement necessary to achieve the target tooth arrangement. The movement path can be optimized based on minimizing the total distance moved, preventing collisions between teeth, avoiding tooth movements that are more difficult to achieve, or any other suitable criteria.

One or more registration features may be added to a digital model of the patient's dental arch for any of the stages of treatment. The registration features may be added to enable the mold to receive an object.

At block 1010, the mold is fabricated based on the determined shape. This may include using a three-dimensional virtual model of the dental arch with the included registration features and sending instructions to a rapid prototyping machine (e.g., a three-dimensional printer) to fabricate the mold. In one embodiment, the mold is fabricated using a rapid prototyping manufacturing technique. One example of a rapid prototyping manufacturing technique is 3D printing. 3D printing includes any layer-based additive manufacturing processes. A 3D printer may receive an input of the 3D virtual model of the mold (e.g., as a computer aided drafting (CAD) file or 3D printable the such as a sterolithography (STL) file), and may use the 3D virtual model to create the mold. 3D printing may be achieved using an additive process, where successive layers of material are formed in proscribed shapes. 3D printing may be performed using extrusion deposition, granular materials binding, lamination, photopolymerization, or other techniques.

In one embodiment, stereolithography (SLA), also known as optical fabrication solid imaging, is used to fabricate an SLA mold. In SLA, the mold is fabricated by successively printing thin layers of a photo-curable material (e.g., a polymeric resin) on top of one another. A platform rests in a bath of a liquid photopolymer or resin just below a surface of the bath. A light source (e.g., an ultraviolet laser) traces a pattern over the platform, curing the photopolymer where the light source is directed, to form a first layer of the mold. The platform is lowered incrementally, and the light source traces a new pattern over the platform to form another layer of the mold at each increment. This process repeats until the mold is completely fabricated. Once all of the layers of the mold are formed, the mold may be cleaned and cured. The manufactured mold may include the registration features for receiving the object that will be fit onto the mold.

At block 1012, an object is attached to the mold. The object may correspond to any of the aforementioned objects. The object may include a registration feature that mates with a registration feature on the mold.

At block 1015, a plastic shell is formed over the mold and the object. This may include sending instructions to a pressure forming or thermoforming machine to cause a sheet of material to be pressure formed or thermoformed over the mold to form a body of the plastic shell. The sheet may be, for example, a sheet of plastic (e.g., an elastic thermoplastic). To thermoform the shell over the mold, the sheet of material may be heated to a temperature at which the sheet becomes pliable. Pressure may concurrently be applied to the sheet to form the now pliable sheet around the breakable mold. Once the sheet cools, it will have a shape that conforms to the mold. An interior shape of the plastic shell substantially conforms to a current or future dental arch of the patient. In one embodiment, a release agent (e.g., a non-stick material) is applied to the mold before forming the plastic shell. This may facilitate later removal of the mold from the plastic shell.

At block 1020, the plastic shell is removed from the object. The object may have one or more retention features such as a taper, slope, lip, ledge, knurling, etc. that causes the object to become mechanically interlocked with the plastic shell after the thermoforming process. Accordingly, the object and the plastic shell may be removed from the mold together. The object may provide structural strength to the plastic shell. The object does not interfere with a fit of the plastic shell onto a dental arch of the patient. The feature of the plastic shell that is formed over the object may enable a force to be applied to at least one of a tooth or a jaw of a patient while the plastic shell is worn on a dental arch of the patient.

In one embodiment, at block 1025 laser welding or ultrasonic welding is performed to bond or fuse the object to the plastic shell. A power and targeting of a laser welding machine or ultrasonic welding machine may be carefully controlled to ensure that only a minimal amount of the object and plastic shell are melted to ensure that a shape of the plastic shell is not degraded. Additionally or alternatively, an adhesive may be applied to the object prior to the thermoforming. The adhesive may act to bond the plastic shell to the object.

In one embodiment, at block 1030 the plastic shell is cut to form a hole and/or a slot into the plastic shell. This may include sending instructions to a cutting machine to cause the cutting machine to cut the plastic shell at specified coordinates. This may permit access through the hole and/or slot to features of the object that is retained in the plastic shell. The cutting machine may be, for example, a laser cutter, plasma cutter or mill. The plastic shell may also be marked and/or trimmed along a gingival cut line.

If the plastic shell is an orthodontic aligner, for example, a set of plastic shells can be fabricated, each shaped to accommodate a tooth arrangement specified by one of the treatment stages, such that the plastic shells can be sequentially worn by the patient to incrementally reposition the teeth from the initial arrangement to the target arrangement. The properties of the plastic shells (e.g., characteristics of features formed in the plastic shells and/or objects retained in or inserted into the plastic shells) can be selected to elicit the tooth movements specified by the corresponding treatment stage. At least some of these properties can be determined via suitable computer software or other digital-based approaches. The fabrication of the plastic shells may involve creating a digital model of the plastic shells to be used as input to a computer-controlled fabrication system.

Figure 11:
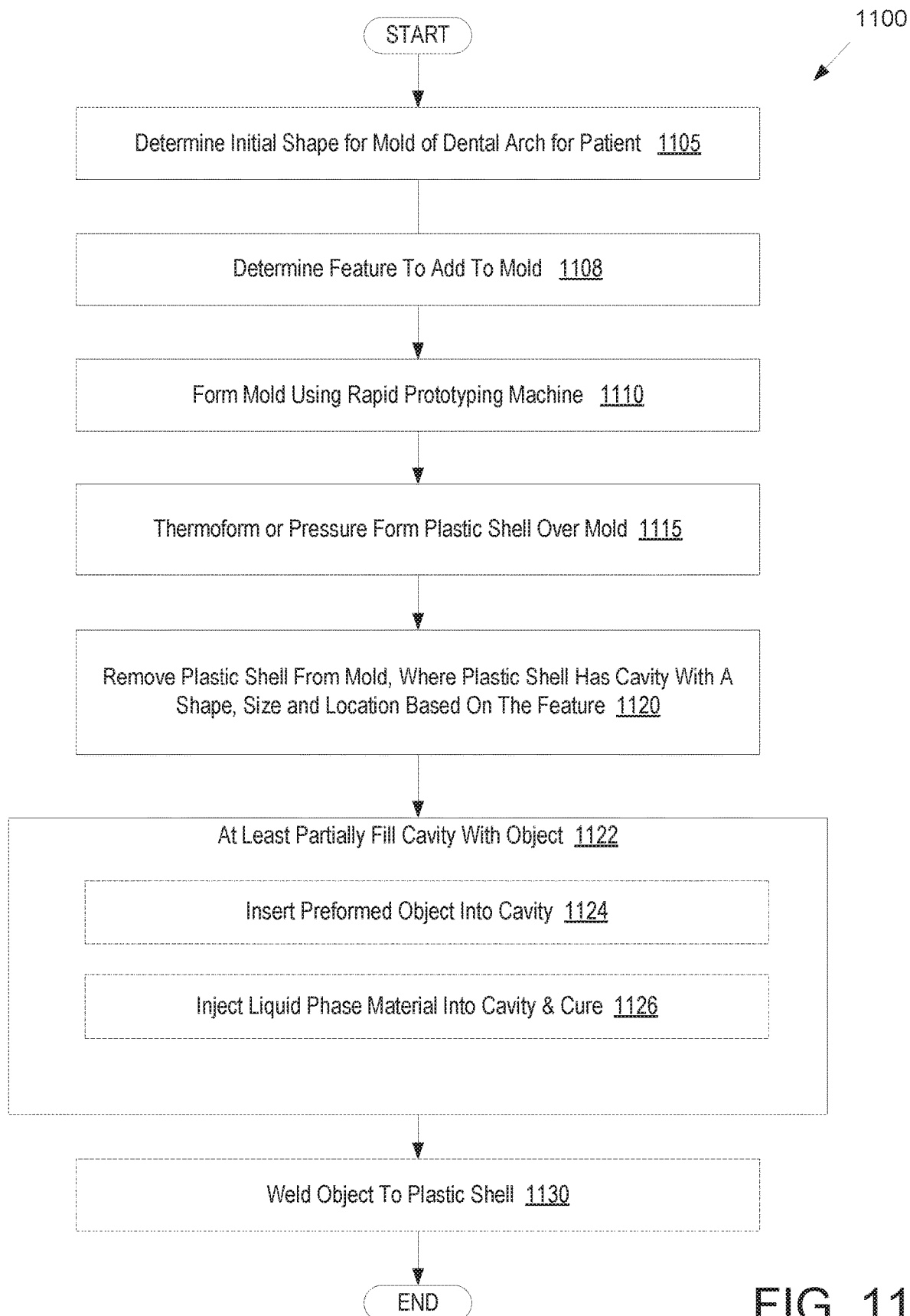
FIG. 11 illustrates a flow diagram of another embodiment for a method of manufacturing plastic shell having hollow feature that is at least partially filled by an object.

FIG. 11 illustrates a flow diagram of another embodiment for a method 1100 of manufacturing a plastic shell having hollow feature that is at least partially filled by an object. In some embodiments, one or more operations of method 1100 are performed by processing logic of a computing device. The processing logic may include hardware (e.g., circuitry, dedicated logic, programmable logic, microcode, etc.), software (e.g., instructions executed by a processing device), firmware, or a combination thereof. For example, one or more operations of method 1100 may be performed by computing device such as computing device 1301 of FIG. 13. Additionally, some operations may be performed by a fabrication machine based on instructions received from processing logic. Some operations may alternately be performed by a user (e.g., based on user interaction with a mold modeling module or drafting program).

At block 1105 of method 1100, a shape is determined for a mold of a dental arch for a patient. The shape may be determined by digitally planning a current, intermediate or final target arrangement of the patient's teeth, and fabricating a mold of a dental arch that reflects that target arrangement. Alternatively, the shape may be determined by taking an impression of a patient's arch and generating a mold from the impression. At block 1108, a feature to add to the mold is determined. The feature may be automatically determined by processing logic or may be manually determined by a user such as a technician. The feature may be any of the features described herein above.

At block 1110, the mold is fabricated based on the determined shape (e.g., based on sending instructions to a rapid prototyping machine). The mold includes the added feature. Forming the mold may include using a three-dimensional virtual model of the dental arch and a rapid prototyping machine (e.g., a three-dimensional printer) to fabricate the mold.

At block 1115, a plastic shell is formed over the mold (e.g., based on sending instructions to a thermoforming or pressure forming machine). In one embodiment, the plastic shell is thermoformed or pressure formed over the mold. Other exemplary methods for fabricating plastic shells include rapid prototyping, stereolithography, or computer numerical control (CNC) milling. The material of the plastic shell can be translucent, such as a translucent polymer. Alternatively, the material may have any other desired color or colors.

At block 1120, the plastic shell is removed from the mold. An interior shape of the plastic shell substantially conforms to a current or future dental arch of the patient. The plastic shell will have a hollow feature that includes a cavity with a shape, size and location based on the feature that was added. The hollow feature may enable a force to be applied to at least one of a tooth or a jaw of a patient while the plastic shell is worn on a dental arch of the patient.

At block 1122, the cavity is at least partially filled with an object. The object has a shape that substantially conforms to a shape or contour of the cavity. The object may provide structural strength to the plastic shell at the location of the hollow feature. The object does not interfere with a fit of the plastic shell onto a dental arch of the patient. Numerous different techniques may be used to fill (or partially fill) the cavity with the object. In one embodiment, at block 1124 a preformed object is inserted into the cavity. In one embodiment, a slot and/or hole are cut into the plastic shell to permit access to the cavity. The preformed object may then be inserted into and/or attached to the feature of the plastic shell that includes the cavity through the slot and/or hole. For example, a sphere attached to a rod may be inserted into a hole cut into the feature.

In one embodiment, at block 1126 a liquid phase material is injected into the cavity in the plastic shell and then cured. The liquid phase material may be injected into the cavity from an underside of the plastic shell. Alternatively, the plastic shell may be placed onto another mold that does not include the added feature. Instead, the other mold may include a shape of a patient's tooth crown at a location corresponding to the location of the feature in the initial mold. In such an embodiment, a hole may be drilled into the feature to provide access to the cavity. The liquid phase material may then be injected into the cavity through the hole. Enough liquid phase material may be injected to fill the cavity. The liquid phase material may contact the tooth crown of the additional mold and conform to a contour of the tooth crown. The liquid phase material may then be cured to transform the liquid phase material into a solid phase material.

In one embodiment, at block 1130 the plastic shell is welded to the object using one of laser welding or ultrasonic welding. Alternatively, an adhesive may be applied to walls of the cavity and/or to the object prior to insertion of the object into the cavity.

Figure 12:
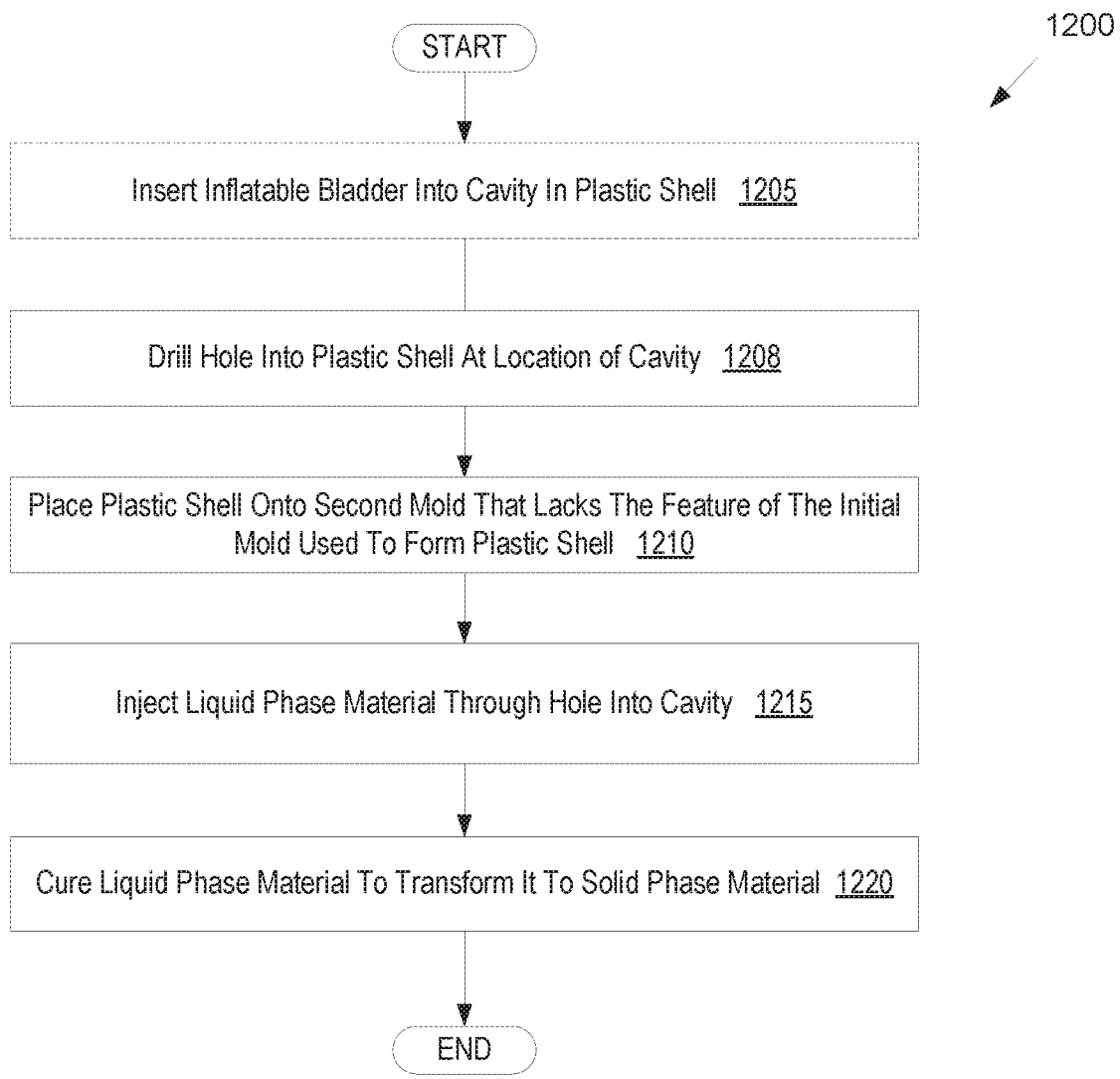
FIG. 12 illustrates a flow diagram of an embodiment for a method of filling a cavity in a hollow feature of a plastic shell.

FIG. 12 illustrates a flow diagram of an embodiment for a method 1200 of filling a cavity in a hollow feature of a plastic shell. In one embodiment, method 1200 is performed at block 1126 of method 1100. At block 1205 of method 1200, an inflatable bladder is inserted into a cavity in a plastic shell. At block 1208, a hole is drilled into the plastic shell at a location of the cavity. The hole may be drilled before or after insertion of the bladder into the cavity.

At block 1210, the plastic shell is placed onto a second mold that lacks a feature of an initial mold that was used to form the plastic shell. The second mold may instead have a tooth crown at a location corresponding to a location of the feature in the initial mold. At block 1215, a liquid phase material is injected into the bladder through the hole in the cavity. The bladder may expand to a shape that conforms to a shape of the cavity and of the tooth crown. At block 1220, the liquid phase material is then cured to transform the liquid phase material into a solid phase material.

Figure 13:
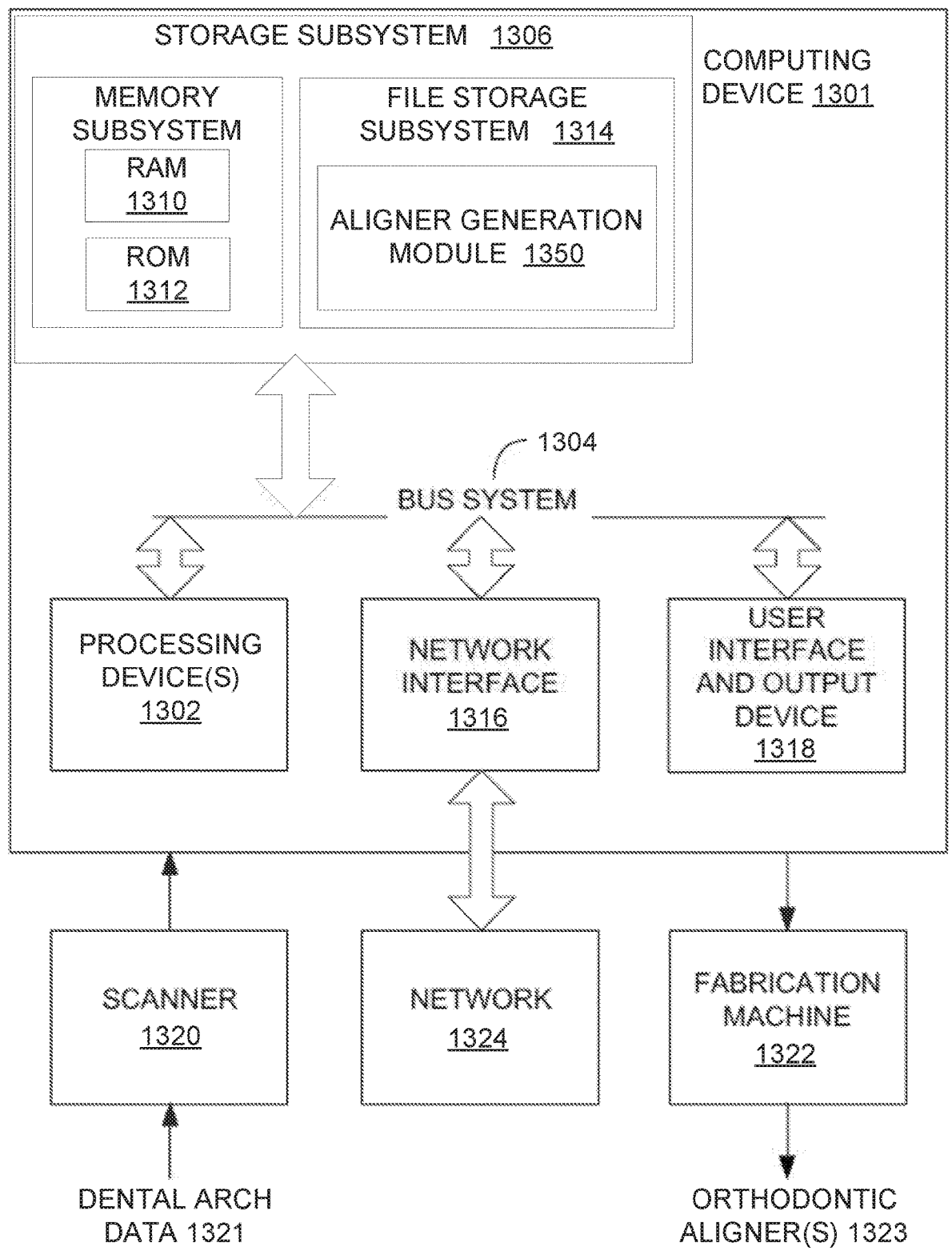
FIG. 13 illustrates a block diagram of an example computing device, in accordance with embodiments of the present invention.

FIG. 13 is a simplified block diagram of a system 1300 that may be used in executing methods and processes described herein. The system 1300 typically includes a computing device 1301 connected to a network 1324, a scanner 1320 and/or a fabrication machine 1322. The computing device 1301 may be connected (e.g., networked) to other machines in a Local Area Network (LAN), an intranet, an extranet, or the Internet. For example, the computing device 1301 may be networked fabrication machine 1322, which may be a rapid prototyping apparatus such as a 3D printer or SLA apparatus. The computing device 1301 may operate in the capacity of a server or a client machine in a client-server network environment, or as a peer machine in a peer-to-peer (or distributed) network environment. The computing device 1301 may be a personal computer (PC), a tablet computer, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. Further, while only a single machine is illustrated, the term computing device shall also be taken to include any collection of machines (e.g., computers) that individually or jointly execute a set (or multiple sets) of instructions to perform any one or more of the methodologies discussed herein.

Computing device 1301 includes at least one processing device 1302 that communicates with one or more peripheral devices via bus subsystem 1304. Processing device 1302 represents one or more general-purpose processors such as a microprocessor, central processing unit, or the like. More particularly, the processing device 1302 may be a complex instruction set computing (CISC) microprocessor, reduced instruction set computing (RISC) microprocessor, very long instruction word (VLIW) microprocessor, processor implementing other instruction sets, or processors implementing a combination of instruction sets. Processing device 1302 may also be one or more special-purpose processing devices such as an application specific integrated circuit (ASIC), a field programmable gate array (FPGA), a digital signal processor (DSP), network processor, or the like. Processing device 1302 is configured to execute the processing logic (instructions) for performing operations and steps discussed herein.

Peripheral devices typically connected to processing device 1302 include a storage subsystem 1306 (memory subsystem 1308 and file storage subsystem 1314), a set of user interface input and output devices 1318, and an interface to outside networks 1316. This interface is shown schematically as "Network Interface" block 1316, and is coupled to corresponding interface devices in other data processing systems via communication network interface 1324.

The user interface input devices 1318 are not limited to any particular device, and can typically include, for example, a keyboard, pointing device, mouse, scanner, interactive displays, touchpad, joysticks, etc. Similarly, various user interface output devices can be employed in a system of the invention, and can include, for example, one or more of a printer, display (e.g., visual, non-visual) system/subsystem, controller, projection device, audio output, and the like.

Storage subsystem 1306 maintains basic programming of the computing device 1301, including computer readable media having instructions (e.g., operating instructions, etc.), and data constructs. The program modules discussed herein are typically stored in storage subsystem 1306. Storage subsystem 1306 typically includes memory subsystem 1308 and file storage subsystem 1314. Memory subsystem 1308 typically includes a number of memories (e.g., random access memory (RAM) 1310, read only memory (ROM) 1312, etc.) including computer readable memory for storage of fixed instructions, instructions and data during program execution, basic input/output system, etc. File storage subsystem 1314 provides persistent (non-volatile) storage for program and data files, and can include one or more removable or fixed drives or media, hard disk, floppy disk, CD-ROM, DVD, optical drives, and the like.

The file storage subsystem 1314 may include a machine-readable storage medium (or more specifically a non-transitory computer-readable storage medium) on which is stored one or more sets of instructions embodying any one or more of the methodologies or functions described herein. A non-transitory storage medium refers to a storage medium other than a carrier wave. The instructions may also reside, completely or at least partially, within the memory subsystem 1308 and/or within the processing device 1302 during execution thereof by the computer device 1301, the memory subsystem 1308 and the processing device 1302 also constituting computer-readable storage media.

The computer-readable storage medium may also be used to store one or more virtual 3D models and/or a plastic shell generation module 1350, which may perform one or more of the operations of methods 900-1100 described with reference to FIGS. 9-11. The term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium other than a carrier wave that is capable of storing or encoding a set of instructions for execution by the machine and that cause the machine to perform any one or more of the methodologies of the present invention. The term "computer-readable storage medium" shall accordingly be taken to include, but not be limited to, solid-state memories, and optical and magnetic media.

One or more of the storage systems, drives, etc. may be located at a remote location, such coupled via a server on a network or via the internet/World Wide Web. In this context, the term "bus subsystem" is used generically so as to include any mechanism for letting the various components and subsystems communicate with each other as intended and can include a variety of suitable components/systems that would be known or recognized as suitable for use therein. It will be recognized that various components of the system can be, but need not necessarily be at the same physical location, but could be connected via various local-area or wide-area network media, transmission systems, etc.

Scanner 1320 includes any means for obtaining a digital representation (e.g., images, surface topography data, etc.) of a patient's teeth (e.g., by scanning physical models of the teeth such as casts, by scanning impressions taken of the teeth, or by directly scanning the intraoral cavity of a patient). Scanner 1320 may receive or generate dental arch data 1321 (which may be data usable to generate a 3D virtual model of a patient's dental arch), and may provide such dental arch data 1321 to computing device 1301. Scanner 1320 may be located at a location remote with respect to other components of the system and can communicate image data and/or information to computing device 1301, for example, via network interface 1324. Fabrication system 1322 fabricates orthodontic aligners 1323 based on a treatment plan, including data set information received from computing device 1301. Fabrication machine 1322 can, for example, be located at a remote location and receive data set information from computing device 1301 via network interface 1324.

It is to be understood that the above description is intended to be illustrative, and not restrictive. Many other embodiments will be apparent upon reading and understanding the above description. Although embodiments of the present invention have been described with reference to specific example embodiments, it will be recognized that the invention is not limited to the embodiments described, but can be practiced with modification and alteration within the spirit and scope of the appended claims. Accordingly, the specification and drawings are to be regarded in an illustrative sense rather than a restrictive sense. The scope of the invention should, therefore, be determined with reference to the appended claims, along with the full scope of equivalents to which such claims are entitled.

What is claimed is:

1. A method comprising:
   attaching an object to a mold of a plurality of teeth of a dental arch, wherein the mold comprises a first registration feature that comprises a protrusion extending from the mold, wherein the object comprises a second registration feature that forms a recess in a central location of a face of the object, and wherein the attaching of the object to the mold comprises interlocking the first registration feature with the second registration feature;
   forming a shell over the mold and the object, wherein the shell comprises:
     a first interior surface forming tooth-receiving cavities that engage with a portion of the mold corresponding to two or more of the plurality of teeth;
     a second interior surface that engages with the object;
     a first exterior surface that is opposite the first interior surface over the portion of the mold; and
     a second exterior surface forming a protruding feature that is opposite the second interior surface over the object and that protrudes from the first exterior surface; and
   removing the shell and the object from the mold, wherein the object is retained inside of the shell, wherein the first exterior surface is opposite the first interior surface without engaging with the mold responsive to the forming of the shell and prior to the removing of the shell and the object from the mold, and wherein the shell is configured to be worn in a mouth of a patient to alter, while the shell is worn in the mouth, contact points between an upper portion and a lower portion of the dental arch of the patient.

2. The method of claim 1, wherein forming the shell over the mold and the object comprises thermoforming or pressure forming the shell over the mold and the object.

3. The method of claim 1, wherein an adhesive is disposed on at least a portion of the object, and wherein the adhesive bonds the shell to the object.

4. The method of claim 1, further comprising:
performing at least one of laser welding or ultrasonic welding to bond the object to the shell.

5. The method of claim 1, wherein the object comprises plastic and the shell comprises a thermoplastic.

6. The method of claim 1, wherein the interlocking comprises sliding the second registration feature over the first registration feature and resting the second registration feature on the first registration feature.

7. The method of claim 1, further comprising:
determining a size and shape of the object based on the dental arch; and
manufacturing the object to have the size and the shape.

8. The method of claim 1, further comprising:
cutting a slot into the shell, wherein the slot is configured to receive and retain at least a portion of an additional object.

9. The method of claim 1, wherein the shell forms a lip, wherein the object has a shape that forms a lower corner, and wherein interaction of the lower corner of the object and the lip of the shell causes the object to be retained inside of the shell.

10. The method of claim 1, wherein the second interior surface abuts the first interior surface, and wherein the first exterior surface abuts the protruding feature.

11. The method of claim 1, wherein the object has one or more retention features to cause the object to be mechanically interlocked with the shell after the forming of the shell.

12. The method of claim 1, wherein the shell comprising the protruding feature is configured to be worn in the mouth to apply forces, while the shell is worn in the mouth, against one or more of the plurality of teeth of the patient to treat malocclusion by moving the one or more of the plurality of teeth of the patient from a first arrangement to a second arrangement while being worn in the mouth.

13. The method of claim 1, wherein:
a first buccal portion of the first interior surface runs from a buccal distal end of the shell to a lip portion of the shell proximate the protruding feature, wherein the first buccal portion is configured to contact at least a portion of buccal surfaces of the two or more of the plurality of teeth; and
a second buccal portion of the first exterior surface corresponds to the at least a portion of buccal surfaces of the two or more of the plurality of teeth, the second buccal portion of the first exterior surface running from the buccal distal end of the shell to the lip portion of the shell proximate the protruding feature.

14. The method of claim 13, wherein the protruding feature is on a buccal side of the dental arch and the protruding feature protrudes from the second buccal portion of the first exterior surface.

15. The method of claim 13, wherein:
a first lingual portion of the first interior surface runs from a lingual distal end of the shell to a first apex portion of the shell corresponding to a top portion of the two or more of the plurality of teeth;
the first lingual portion is configured to contact at least a portion of lingual surfaces of the two or more of the plurality of teeth;
a second lingual portion of the first exterior surface corresponds to the at least a portion of lingual surfaces of the two or more of the plurality of teeth, the second lingual portion of the first exterior surface running from the lingual distal end of the shell to the first apex portion of the shell;
the shell has a first approximately uniform thickness between the first lingual portion of the first interior surface and the second lingual portion of the first exterior surface from the lingual distal end of the shell to the first apex portion of the shell;
the shell has the first approximately uniform thickness between the second exterior surface forming the protruding feature and the second interior surface;
the protruding feature extends to a second apex portion of the shell corresponding to a top of the object that is at a first height that is greater than a second height of the first apex portion of the shell corresponding to the top portion of the two or more of the plurality of teeth;
a first portion of the second interior surface runs from the first apex portion of the shell to the second apex portion of the shell;
a second portion of the second exterior surface runs from the first apex portion of the shell to the second apex portion of the shell; and
the first approximately uniform thickness between the second exterior surface and the second interior surface runs from the first apex portion of the shell to the second apex portion of the shell.

16. The method of claim 15, wherein:
a third portion of the second interior surface runs from the second apex portion of the shell to the lip portion of the shell proximate the protruding feature;
a fourth portion of the second exterior surface runs from the second apex portion of the shell to the lip portion of the shell proximate the protruding feature;
the shell has the first approximately uniform thickness between the second exterior surface and the second interior surface from the second apex portion of the shell to the lip portion of the shell proximate the protruding feature;
the shell has the first approximately uniform thickness between the first buccal portion of the first interior surface and the second buccal portion of the first exterior surface from the buccal distal end of the shell to the lip portion of the shell proximate the protruding feature; and
the lip portion of the shell proximate the protruding feature has a thickness that is greater than the first approximately uniform thickness, the lip portion forming a lip to retain the object.

17. A plastic shell comprising:
a first interior surface forming tooth-receiving cavities that substantially conform to a plurality of teeth of a dental arch of a patient;
a first exterior surface that is opposite the first interior surface;
a hollow protruding feature comprising a second interior surface that forms a cavity, and a second exterior surface that is opposite the second interior surface and that protrudes from the first exterior surface; and an object inserted into the cavity, wherein the object provides structural strength to the plastic shell at a location of the hollow protruding feature and does not interfere with a fit of the plastic shell onto the dental arch of the patient, wherein the object comprises an object registration feature that forms a recess in a central location of a face of the object, wherein the object registration feature is configured to interlock with a mold registration feature of a mold, wherein the mold registration feature comprises a protrusion extending from the mold, and wherein the plastic shell is configured to be worn in a mouth of the patient to alter, while the plastic shell is worn in the mouth, contact points between an upper portion and a lower portion of the dental arch of the patient.

18. The plastic shell of claim 17, wherein at least one of a retention feature or a geometry of the cavity and of the object that fills the cavity cause the object to be mechanically retained inside of the cavity.

19. The plastic shell of claim 17, wherein the object is bonded to the plastic shell.

20. The plastic shell of claim 17, wherein the object registration feature is configured to interlock with the mold registration feature of the mold by sliding the object registration feature of the object over the mold registration feature of the mold and resting the object registration feature on the mold registration feature.

* * * * *